United States Patent
Schiestl (10) Patent No.: US 6,264,915 B1
(45) Date of Patent: *Jul. 24, 2001

(54) PROCESS FOR DETECTING POTENTIAL CARCINOGENS

(75) Inventor: Robert H. Schiestl, Boston, MA (US)

(73) Assignee: The President and Fellows of Harvard College, Cambrige, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/958,054

(22) Filed: Oct. 27, 1997

Related U.S. Application Data (63) Continuation-in-part of application No. 08/266,014, filed on Jun. 27, 1994, now Pat. No. 5,762,908, which is a continuation-in-part of application No. 07/929,293, filed on Sep. 13, 1992, now abandoned.

(51) Int. Cl.$^7$ .......................... A61K 49/00; A01K 67/00; C12N 15/00; C12N 15/63

(52) U.S. Cl. .......................... 424/9.2; 424/9.1; 424/9.8; 435/440; 435/455; 800/8

(58) Field of Search .................. 424/9.1, 9.2, 9.8; 435/320.1, 172.3, 4, 5, 6, 440, 455; 800/3, 13, 14, 18, 8

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,701,406 | 10/1987 | Chou . |
| 4,736,866 | 4/1988 | Leder et al. . |
| 4,800,195 | 1/1989 | Burgess et al. . |
| 4,873,191 | 10/1989 | Wagner et al. . |
| 4,965,188 | 10/1990 | Mullis et al. . |
| 4,968,633 | 11/1990 | Marcucci . |
| 4,997,757 | 3/1991 | Schiestl . |
| 5,021,335 | 6/1991 | Tecott et al. . |
| 5,028,525 | 7/1991 | Gray et al. . |
| 5,175,383 | 12/1992 | Leder et al. . |
| 5,175,384 | 12/1992 | Krimpenfort et al. . |
| 5,175,385 | 12/1992 | Wagner et al. . |
| 5,221,778 | 6/1993 | Byrne et al. . |
| 5,288,846 | 2/1994 | Quertermous et al. . |
| 5,298,422 | 3/1994 | Schwartz et al. . |
| 5,347,075 | 9/1994 | Sorge . |
| 5,360,735 | 11/1994 | Weinshank et al. . |
| 5,387,742 | 2/1995 | Cordell . |
| 5,464,764 | 11/1995 | Capecchi et al. . |
| 5,487,992 | 1/1996 | Capecchi et al. . |
| 5,614,396 | 3/1997 | Bradley et al. . |
| 5,762,908 | * 6/1998 | Schiestl ................ 424/9.1 |

FOREIGN PATENT DOCUMENTS

| | | |
|---|---|---|
| 93/14200 | 7/1993 | (WO) . |
| 94/06908 | 3/1994 | (WO) . |
| 94/23049 | 10/1994 | (WO) . |
| 94/28123 | 12/1994 | (WO) . |

OTHER PUBLICATIONS

Bradley et al. Modifying the mouse: Design and desire. Bio/Technolgy 10: 534–539, May 1992.*

Campbell and Wilmut. Totipotency or multipotentiality of cultured cells: Applications and progress. Theriogenology 47: 63–72, Jan. 1997.*

Wall, R.J. Transgenic livestock: Progress and prospects for the future. Theriogenology 45: 57–68, May 1992.*

Abelson, P.H. (1994) Risk assessment of low–level exposures. Science 265:1507.

Agurell, et al., (1991) Genotoxic effects of ethylene oxide and propylene oxide: a comparative study, Mutat. Res., 250, 229–237.

Ames and Gold (1990) Too many rodent carcinogens: Mitogenesis increases mutagenesis. Science 249:970–971.

Aubrecth et al. (1995) Carcinogens induce intrachromosomal recombination in human cells. Carcinogenesis 16(11):2841–2846.

Biard, et al. (1992) Regulation of the *Escherichia coli* lac operon expressed in human cells. Bioch. Biophys. Acta 1130:68–74.

Blochinger and Diggelman (1984) Hygromycin B phosphotransferase as a selectable marker for DNA transfer experiments with higher eucaryotic cells. Mol Cell Biol. 4(12):2929–31.

Brennan et al., (1994) Oxidative mutagenes induce intrachromosomal recombination in yeast. Mut. Res. 308:159–167.

(List continued on next page.)

Primary Examiner—Jill D. Martin
Assistant Examiner—Anne-Marie Baker
(74) Attorney, Agent, or Firm—Kohn & Associates

(57) ABSTRACT

A process for screening an agent to determine its effect upon the frequency of genome rearrangement in transgenic mammals. The process comprises the steps of: (a) providing a transgenic mammal into which repeated genetic elements have been inserted into its haploid genome. The repeated genetic elements are sufficiently homologous so that, under ambient conditions, they recombine with each other and give rise to an identifiable genome rearrangement at a rate of at least about $1 \times 10^{-11}$ occurrences per cell per generation. In a preferred embodiment the rearrangement can be identified as a phenotypic event or by PCR. The process further comprises (b) exposing at least one of the transgenic mammals to the agent to be tested, thereby providing an exposed mammal and (c) determining the extent of genome rearrangement which exists in a first exposed animal selected from the group consisting of the exposed mammal, its offspring, and mixtures thereof. The process then (d) compares the extent of genome rearrangement existing in the first animal with the extent of genome rearrangement existing in a second unexposed mammal and the offspring of the unexposed control mammals, and mixtures thereof.

1 Claim, 1 Drawing Sheet

OTHER PUBLICATIONS

Brenner, et al., (1989) Analysis of mammalian cell genetic regulation in situ by using retrovirus derived "portable exons" carrying the *Escherichia coli* lacZ gene. Proc. Natl. Acad. Sci. USA 86:5517–5521.

Brilliant, et al., (1991) Direct molecular identification of the mouse pink–eyed unstable mutation by genome scanning. Science 252:566–569.

Burke and Olson, "Preparation of Clone Libraries in Yeast Artificial–Chromosome Vectors" in *Methods in Enzymology*, vol. 194, "Guide to Yeast Genetics and Molecular Biology", eds. C. Guthrie and G. Fink, Academic Press, Inc., Chap. 17, pp. 251–270 (1991).

Calabretta, et al., (1982) Genome intability in a region of human DNA enriched in Alu repeat sequences. Nature 296:219–225.

Capecchi, "Altering the genome by homologous recombination" *Science* 244:1288–1292 (1989).

Carls and Schiestl (1993) Evaluation of the yeast DEL assay with ten compounds selected by the International Program on Chemical Safety for evaluation of short term tests for carcinogens. Mutation Research 320:293–303.

Copeland et al. (1983), Excision of the DBA ectopic provirus in dilute coat–color revertants of mice occurs by homologous recombination involving the viral LTRs, Cell 33:379–387.

Cortopassi, et al., (1992) A pattern of accumulation of a somatic deletion of mitochondrial DNA in aging human tissues. Proc. Nat. Acad. Sci. USA89:7370–7374.

Davies et al., "Targeted alterations in yeast artificial chromosomes for inter–species gene transfer", *Nucleic Acids Research*, vol. 20, No. 11, pp. 2693–2698 (1992).

Dickinson et al., "High frequency gene targeting insertional vectors", *Human Molecular Genetics*, vol. 2, No. 8, pp. 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Friedrich and Soriano (1991) Promoter traps in embryonic stem cells: A genetic screen to identify and mutate developmental genes in mice. Genes and Development 5:1513–1523.

Galli and Schiestl, (1995) Salmonella test positive and negative carcinogens show different effects on intrachromosomal recombination in $G_2$ cell cycle arrested yeast cells. Carcinogenesis 16(3):659–663.

Gardner, et al. (1992) The mouse pink–eyed dilution gene: Association with human Prader–Willi and Angelmann Syndromes. Science 257:1121–1124.

Gondo, et al., (1993) High–frequency genetic reversion mediated by a DNA duplication: The mouse pink–eyed unstable mutation. Proc. Natl. Acad. Sci. USA 90:297–301.

Gordon, 1989. Transgenic Animals. Intl. Rev. Cytol. 115:171–229.

Gunz et al. "Can Nongenotoxic Carcinogens Be Detected With the lacI Transgenic Mouse Mutation Assay" disclosed (at p. 209).

Heddle, et al. (1983) The induction of micronuclei as a measure of genotoxicity. A report of the U.S. Evironmental Protection Agency Gene–Tox Program. Mutat. Res. 123:61–118.

Huxley et al., "The human HPRT gene on a yeast artificial chromosome is functional when transferred to mouse cells by cell fusion", *Genomics*, 9:742–750 (1991).

Jakobovits et al., "Germ–line transmission and expression of a human–derived yeast artificial chromosome", *Nature*, vol. 362, pp. 255–261 (1993).

Jeffreys et al. (1985). Hypervariable "minisatellite" regions in human DNA. Nature 314:67.73.

Jelinek et al. (1982), Repetitive sequences in eukaryotic DNA and their expression. Annual Review of Biochemistry, 51:813–844. [page numbers were incorrectly cited in application].

Kuehn et al., (1987) A potential animal model for Lesch–Nyhan syndrome through introduction of HPRT mutations into mice. Nature 326:295–298.

Lamb et al., "Introduction and expression of the 400 kilobase precursor amyloid protein gene in transgenic mice", *Nature Genetics*, vol. 5, pp. 22–29 (1993).

Lavitrano et al, 1989. Sperm Cells as Vectors for Introducing Foreign DNA into Eggs: Genetic Transformation of Mice. Cell 57:717–723.

Lo, 1983. Transformation by Iontophoretic Microinjection of DNA: Multiple Integrations Without Tandem Insertions. Mol. Cell. Biol. 3:1803–1814.

Mansour (1990). Gene Targeting in Murine Embryonic Stem Cells: Introduction of Specific Alterations into the Mammalian Genome. GATA 7(8):219–227.

Melvold (1971). Spontaneous Somatic Reversion in Mice Effects of Parental Genotype on Stability at the p–Locus. Mutation Research 12:171–174.

Mirsalis, et al. (1992) Toxicologist 12, 53.

Mirsalis,(1993a). Effects of nongenotoxic carcinogens or hepatic mutations in lacI transgenic mice, Environ. Mol. Mutagen. 21[22]:48.

Mirsalis, et al. (1993b). Induction of hepatic mutations in lacI transgenic mice, Mutagenesis, 8,(3):265–271.

Monnat, et al., (1992) Molecular Structure and Genetic Stability of Human Hypoxanthine Phosphoribosyltransferase (HPRT) Gene Duplications. Genomics 13:788–796.

Moore, et al., (1990) Interaction of the murine dilute suppressor gene (dsu) with fourteen coat mutations. Genetics 125:421–430.

Murti et al., (1992) High frequency of germ line gene conversion in transgenic mice. Mol. Cell. biol. 12:2545–2552.

Murti, et al. (1994) A recombination based transgenic mouse system for genotoxicity testing. Mutat. Res. 307:583–595.

Nagy, et al. (1993) Derivation of completely cell culture derived mice from early–passage embryonic stem cells. Proc. Natl. Acad. Sci. USA 90:8424–8428.

Nolan et al., (1988) "Fluorescence–activated cell analysis and sorting of viable mammalian cells based on beta–D–galactosidase activity after transduction of *Escherichia coli* lacZ" PNAS USA 85:2603–2607.

Paulson et al. (1985), A transposon–like element in human DNA, Nature 316:359–361. [Volume and page numbers were incorrectly cited in application].

Pearson and Choi, Expression of the human b–amyloid precursor protein gene from a heast artificial chromosome in transgenic mice. Proc. Natl. Scad. Sci. USA, 90:10578–82.

Rannug, et al. (1992) Certain tryptophan photoproducts are inhibitors of cytochrome P450–dependent mutagenicity, Environm. and Molec. Mutagen., 20, 289–296.

Reaume et al., 1996, Enhanced amyuloidogenic processing of the b–amyloid precursor protein in gene–targeted mice bearing the Swedish familial Alzheimer's disease mutations and a "humanized" Ab sequence. *J. Biol. Chem.* 27(38):23380–23388.

Rothstein, "Targeting, disruption, replacement, and allele rescue: integrative DNA transformation in yeast" in *Methods in Enzymology*, vol. 194, "Guide to Yeast Genetics and Molecular Biology", eds. C. Guthrie and G. Fink, Academic Press, Inc., Chap. 19, pp. 281–301 (1991).

Russell and Russell (1954) An analysis of the changing radiation response of the developing mouse embryo. J. Cellular Comp. Physiol. 43:103–149.

Russell, et al. (1981) Use of the mouse spot test in chemical mutagenesis: Interpretation of past data and recommedation for future work. Mutation Res. 86:355–379.

Schedl et al., "A yeast artificial chromosome covering the tyrosinase gene confers copy number–dependent expression in transgenic mice", *Nature*, vol. 362, pp. 258–261 (1993).

Schiestl, (1989) Nonmutagenic carcinogens induced intrachromsomal recombination in yeast. Nature 337. 285–288.

Schiestl et al.,(1989) Carcinogens induce intrachromosomal recombination in yeast. Carcinogenesis 10:1445–1455.

Schiestl et al., (1994) Reversion of the mouse pink–eyed unstable mutation induced by low doses of X–rays. Science 266:1573–1576.

Schiestl et al. (1997a) Carcinogens induce reversion of the mouse pink–eyed unstable mutation. PNAS 94:4576–4581.

Schiestl and Prakash, (1988) RAD1, an excision repair gene of *Saccharomyces cerevisiae*, is also involved in recombination. Mol. Cell. Biol. 8:3619–3626.

Schlager et al. (1967) Spontaneous mutation and mutation rates in the house mouse.

Schmid et al. (1989) In .Adolph, K.W. (ed.), Chromosomes: Eukaryotic, Prokaryotic and Viral., CRC Press, Boca Raton, vol. I, pp. 3–29.

Searle and Stephenson (1982) An in vivo method for the detection of somatic mutations at the cellular in mice. Mutat. Res. '92:205–215.

Seperak et al. (1988), Somatic and germ–line reverse mutation rates of the retrovirus–induced dilute coat–color mutation of DBA mice, PNAS USA 85:189–192.

Singer (1982), SINEs and LINES: Highly repeated short and long interspersed sequences in mammalian genomes, Cell 28, 433–434.

Sommers, (1995) Induction of DEL recombination in the yeast *Saccharomyces cerevisiae* using microtiter plate assay format. In Vitro Toxicology. 8(1):37–47.

Soong, et al. (1992) Mosaicism for a specific somatic mitochondrial DNA mutation in adult human brain. Nature Genetics 2:318–323.

Stout and Caskey (1985) HPRT: gene structure, expression, and mutation. Annu. Rev. Genet. 19, 127–148.

Strauss et al., "Germ line transmission of a yeast artificial chromosome spanning the murine $a_1$ (I) collagen locus", *Science*, vol. 259, pp. 1904–1907 (1993).

Styles and Penman (1985) The mouse spot test, evaluation of its performance in identifying chemical mutagens and carcinogens. Mutation Res. 154:183–204.

Tao, PNAS 90:10681–85 (1993) [n/a—will mail in].

Thacker, (1992). Radiation induced mutation in mammalian cells at low doses and low dose rates. Advances in Radiation Biology, 16:77–124.

Thomas and Capecchi (1987) Site–directed mutagenesis by gene targeting in mouse embryo–derived stem cells. Cell 51:503–512.

Thompson et al, 1989. Germ Line Transmission and Expression of a Corrected HPRT Gene Produced by Gene Targeting in Embryonic Stem Cells. Cell 56:313–321.

Weinstein, (1991) Mitogenesis is only one factor in carcinogenesis. Science 251:387–388.

Van Der Putten et al., 1985. Efficient insertion of genes into the mouse germ line via retroviral vectors. PNAS USA 82:6148–6152.

Yang, et al. (1988) Spontaneous reversion of novel Lesch–Nyhan mutation by HPRT gene rearrangement. Somat Cell Mol Genet. 14(3):293–303. [n/a—will main in].

Zakany et al. (1990) The use of lacZ gene fusions in the studies of mammalian development: developmental regulation of mammalian homeobox genes in the CNS. J. Physiol., Paris, 1990, 84:21–26. [n/a—will main in].

Zhang and Jenssen (1992) Reversion of the hprt mutant clone SP5 by intrachromosomal recombination. Carcinogenesis, 13, 609–615. [n/a—will main in].

Kohler et al. Spectra of spontaneous and mutagen–induced mutations in the lacI gene in transgenic mice. Proc. Natl. Acad. Sci. USA 88:7958–7962, Sep. 1991.*

Gossen et al. Efficient rescue of intergrated shuttle vectors from transgenic mice: A model for studying mutations in vivo. Proc. Natl. Acad. Sci. USA 86:7971–7975, Oct. 1989.*

Albertini et al. Alterations of the hprt gene in human in vivo–derived 6–thioguanine–resistant T lymphocytes. Nature 316:369–371, Jul. 25, 1985.*

Brilliant et al. Direct molecular indentification of the mouse pink–eyed unstable mutation by genome scanning. Science 252:566–569, Apr. 26, 1991.*

Mansour, SL Gene targeting in murine embryonic stem cells: Introduction of specific alterations into the mammalian genome. GATA 7(8):219–227, 1990.*

Copeland et al. Excision of the DBA ecotropic provirus in dilute coat–color revertants of mice occurs by homologous recombination involving the viral LTRs. Cell 33:379–387, Jun. 1983.*

Tang et al. Carcinogen activation by human liver enzymes in the Ames mutagenicity test. Mutation Research 46(6):387–394, 1977.*

* cited by examiner

PROCESS FOR DETECTING POTENTIAL CARCINOGENS

CROSS REFERENCE TO RELATED APPLICATIONS

This application is a Continuation-In-Part of U.S. Ser. No. 08/266,014, filed Jun. 27, 1997, now U.S. Pat. No. 5,762,908, which was a Continuation-in-Part of U.S. Ser. No. 07/929.293, filed Sep. 13, 1992, now abandoned.

GOVERNMENT SUPPORT

Not applicable

BACKGROUND OF THE INVENTION

1. Field of the Invention

The present invention is related to assays for identifying potential carcinogens. More specifically, the present invention provides a transgenic animal model in which to test potential carcinogens.

2. Description of the Related Art

Assays for identifying potential carcinogens are well known to those skilled in the art; see, e.g., U.S. Pat. No. 4,997,757, the entire disclosure of which is hereby incorporated by reference into this specification.

The assay described in U.S. Pat. No. 4,997,757 utilizes a viable strain of the unicellular yeast *Saccharomyces cerevisiae*; and the process of this patent is substantially superior to other potential carcinogen screening assays utilizing yeast or Salmonella.

Cancer is a disease affecting mammals; and an assay utilizing mammals is commonly believed to be superior to assays which utilize non-mammalian organisms (such as yeast, or Salmonella). Data generated from mammalian assays are generally more accepted than data generated from non-mammalian assays. One reason for this is that mammalian cells and body fluids contain enzymes some of which metabolize xeno-biotic agents and sometimes produce carcinogenic metabolites. These enzymes are not present to the same extent and in the same variety in non-mammalian systems; and, thus, to simulate a mammalian system with a non-mammalian assay mammalian liver homogenate must be added during the test. This not only adds a substantial amount of cost and time to the non-mammalian assay, but it is not clear that the mammalian liver homogenate accurately reflects the environment within the mammal.

There are several prior art processes for detecting the presence of carcinogens or potential carcinogens which utilize mammals; these are often referred to as "long term bioassays". In one such process a colony of mice is exposed to an agent and, after a substantial period of time, the occurrence of tumors is noted and evaluated. An example of such a process is disclosed in U.S. Pat. No. 4,736,866 of Leder, the disclosure of which is hereby incorporated into this specification. One of the problems with this type of process is the relatively long period of time which must be allowed for the tumor to develop after the mice have been exposed to the agent; after this period of time, each mouse in the test must be killed and subjected to an autopsy to evaluate the presence of the tumors. Furthermore, in this process, a large number of mice must be used. For instance, long term carcinogenesis studies require groups of 50 animals per dose for each of three doses, per sex for both sexes and per species for mice and rats. $LD_{50}$ studies may require as many as 50 animals per dose, for four or more doses (see generally Lu Basic Toxicology, $2^{nd}$ Edition, eds Taylor and Francis, Bristo, Pa., 1991). Additionally many of these assays require two years of exposure and one year or more of data gathering and evaluation for the long term carcinogenicity studies. Because of these factors, the assays are prohibitively expensive allowing only a few chemicals to be tested per year.

Further, for the long term studies high doses are required to obtain significant results (maximum tolerated dose experiments). This has led to widespread criticism of long term studies which culminated in questions about the validity of the entire program (e.g. Ames and Gold 1990; Weinstein 1991, "Carcinogenesis mechanism, the debate continues" letters, Science 252:902–904, 1991 and many public meetings to which both experts were invited, newspaper articles etc.; Abelson, 1994).

In an editorial, Abelson (1994) criticized the high dose experiments. The letters in response to this editorial (Science 266:1141–1145, 1994) are a good example of the current knowledge or lack thereof in the field. The only data that were cited in this debate are a limited number of examples on dose responses for carcinogenesis. A number of possible theories supporting or contradicting linear dose responses were cited without a single mechanistic example of data supporting those theories. This lack of data is currently splitting researchers into schools of different theories greatly limiting the public acceptance of current methods in risk assessments.

Furthermore, because of the high doses and the long term exposure, there is considerable public concern about the suffering of a large number of animals. In addition, in most cases a comparison of in vivo to in vitro results is not possible since different endpoints and different systems are being used. For many of these assays the measured endpoint is death, tumors per mouse etc. without much information about the mechanism of the toxicity. However, mechanistic information is required for our understanding of the toxic response which is essential for risk assessment and for prevention.

There is an assay which attempts to respond to the above criticisms, the "mouse spot test," which does not require the autopsies of a large number of-dead mice. This test is described in a review (Styles and Penman, 1985). In this test, a multiplicity of pregnant mice are exposed to the agent to be tested, and the offspring of such mice are then evaluated to determine the presence of spots in their coats. There is some correlation between the presence of such spots and the carcinogenicity of the agent tested. However the correlation is relatively poor.

As is indicated in U.S. Pat. Nos. 4,701,406 and 4,997,757, incorporated herein by reference, the well-known Ames assay (which utilizes certain mutant strains of bacteria) has several major disadvantages. Many classes of carcinogenic compounds consistently show poor responses in the Ames assay. The Ames assay is not very useful for evaluating certain metals, steroid hormones, and chlorinated hydrocarbons which although they are known to be carcinogens, give very poor responses in this assay. Also, the Ames assay is not generally useful for evaluating carcinogenic compounds which are not mutagenic; see, e.g., column 2 of U.S. Pat. No. 4,997,757.

It appears, however, that, notwithstanding the well-known shortcomings of the Ames assay, the mouse spot test is inferior to such assay. In several experiments (Styles and Penman, 1985) 45 known carcinogens and 6 known non-carcinogens were evaluated in both the Ames assay and the mouse spot test. The Ames assay correctly identified 84 percent of these agents; however, the mouse spot test correctly identified only 74 percent of these agents.

Currently, there is available a second mouse assay system: the "Big Blue™ Transgenic Mouse Mutagenesis Assay System," which is marketed by the Stratagene Company 11099 North Torrey Pines Road, La Jolla, Calif. According to Stratagene, this system utilizes a transgenic mouse lineage of the inbred strain C57BL/6 such that each cell of every mouse in the line contains multiple copies of a bacteriophage lambda shuttle vector which is approximately 43 kilobases in size (Mirsalis et al., 1993b).

The Stratagene system, however, has several distinct shortcomings. In the first place, it does not detect certain powerful carcinogens detectable by other assays. As shown by Mirsalis et al (1993b) transgenic B6C3F1 and C57BL/6 mice containing a lambda shuttle vector containing a lacI target do not detect the carcinogenic activity of methylmethane sulfate. (Methylmethane sulfate is a known hepatocarcinogen which does not induce mutation types which are detected by the Stratagene assay in the livers of such mice). Further, Mirsalis et al. (1993a) indicates that five daily administrations of carbon tetrachloride to such mice produced no increase in hepatic mutant frequency in Stratagene mice (lacI mouse).

The consensus among those in the molecular toxicology field appears to be that non-genotoxic carcinogens are not detectable by the Stratagene assay system. In Gunz et al. (at page 209) it is noted that "The negative results, both for lacI mutations in liver DNA and for the rate of hepatocyte division, show that the non-genotoxic carcinogens investigated do not give rise to a generally increased level of mutations or a sustained general increase in the rate of cell division".

It is known that the Stratagene mouse assay system is not very sensitive to ionizing radiation (Tao, et al. 1993). This is a critical shortcoming, since exposure to ionizing radiation constitutes a major health hazard. Thus, as was stated by J. Thacker (1992), "It is a sobering thought that, more than 60 years after the demonstration by Muller of the mutagenic effect of ionizing radiation, questions concerning the estimation of risk to the human population are still before us. This lack of progress is not through lack of effort but rather through the complexity of the task and the need to develop and refine methods of analysis".

Applicant has provided in U.S. Pat. No. 5,762,908 and assigned to the same assignee and incorporated herein in its entirety by reference, an improved method of evaluating carcinogens, including ionizing radiation, in mice. In the assay two alleles of a gene duplication, the pink-eyed unstable, ($p^{un}$) mutation in the mouse are used to score for genomic rearrangement in response to exposure. The $p^{un}$ mutation causes a dilution of the pigment in coat-color and eye color and is due to a deletion disruption of the pink-eyed dilute locus creating a DNA sequence duplication of about 75 kb which is a head to tail duplication (Brilliant et al. 1991, Gondo et al. 1993). Reversion of this mutation is easily scorable as black spots on the dilute coat and is due to a deletion of one copy of the duplicated sequence resulting in production of wildtype melanin in melanocytes. The frequency of reversion of the $p^{un}$ mutation is uniquely sensitive towards the effects of x-rays. $p^{un}$ reversion events are also inducible by the Salmonella-assay-positive carcinogens EMS, MMS, ENU and benzo(a)pyrene as well as with the Salmonella-assay-negative carcinogens trichloroethylene, benzene and sodium arsenate. Most of these same chemicals are positive in the yeast deletion (DEL) assay (Schiestl 1989; Carls and Schiestl 1993) and those that have been tested are also positive in the human cell culture deletion assay.

However, while the $p^{un}$ reversion assay is a significant improvement as shown in the Examples of the co-pending application, '908 patent, it still has disadvantages. The assay is based on the induction of deletions in the embryo. Thus, the chemicals have to be able to enter through the placenta. Permeability of the placenta will differ from chemical to chemical. In addition, embryos may be much more sensitive to the toxic effects of chemicals and thus may die and be aborted rather than give scorable results. Further, quantitative PCR cannot be used to quantify deletion events which have been shown to be associated with the reversion phenotype in spontaneously revertant mouse (Gondo et al., 1993; Gardner et al., 1992). PCR also cannot be used for detection on the genomic level since $p^{un}$ contains a tandem duplication and the primers to detect the revertant would have to be placed on each side of the duplication in the unique sequence and it is not possible to amplify a 75 kb piece of DNA. Further, the p gene is only expressed in melanocytes, eyes, and gonades (Gardner 1992). Thus, tissue specific effects in other tissues cannot be studied.

It is an object of this invention to provide a toxicology assay utilizing mice which is capable of detecting the toxic effects of mutagenic carcinogens such as, e.g., methyl methane sulfonate, ethyl methane sulfonate, benzo(a)pyrene, ethylnitrosourea, and the like in any tissue in vivo in mice.

It is another object of this invention to provide a toxicology assay utilizing mice which is capable of detecting the toxic effects of nonmutagenic carcinogens such as, e.g., carbon tetrachloride, trichloroethylene, benzene, sodium arsenate, and the like in any tissue in vivo in adult mice.

It is an object of this invention to provide a mammalian assay for detecting potential carcinogens which utilizes mammals but does not require their autopsy.

It is yet another object of this invention to provide a mammalian assay for detecting potential carcinogens which can be completed in substantially shorter period of time than that required for long term bioassays.

It is yet another object of this invention to provide a mammalian assay for detecting potential carcinogens which, in at least some respects, is more accurate than prior art mammalian assays and more accurately mimics the human sensitivity.

SUMMARY OF THE INVENTION

According to the present invention, a process for screening an agent to determine its effect upon the frequency of genome rearrangement in transgenic mammals and therefore its carcinogenic potential is disclosed. The process comprises the steps of: (a) providing a transgenic mammal into which repeated genetic elements have been inserted into its haploid genome. The repeated genetic elements are sufficiently homologous so that, under ambient conditions, they recombine with each other and give rise to an identifiable genome rearrangement at a rate of at least about $1 \times 10^{-11}$ occurrences per cell per generation. In a preferred embodiment the rearrangement can be identified as a phenotypic event (change in a phenotypic expression) or by PCR. The process further comprises steps (b) exposing at least one of the transgenic mammals to the agent to be tested, thereby providing an exposed mammal and (c) determining the extent of genome rearrangement which exists in a first exposed animal selected from the group consisting of said exposed mammal, its offspring, and mixtures thereof. The process then (d) compares the extent of genome rearrangement existing in the first animal with the extent of genome rearrangement existing in a second control unexposed mammal and the offspring of the unexposed control mammals, and mixtures thereof.

The present invention also provides for the use of the transgenic assays in toxicology that will lead to a reduction in the number of animals and assays that require much less time. The combination of these two factors will make the use of the transgenic mouse assays much less expensive than current assays. This in turn will lead to the ability of using more doses and establishing dose response relations. The molecular mechanism and the initiating lesion resulting in the deletion events can be studied and may give some mechanistic information as to the biological activity of the carcinogens. Since the same constructs will be available in tissue culture cells, the correlation between in vivo and in vitro results can be directly determined. This could potentially lead to a more widespread use of the tissue culture assays further reducing the number of animals needed.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

The present invention provides a process for detecting a potential carcinogen. In the first step of this process, a mammal which contains a selected repeated genetic element (DEL Construct; DEL Substrate) in its haploid genome is provided. In a preferred embodiment the mammal is engineered to carry the repeated genetic element. The repeated genetic element in the mammal's haploid genome is selected such that it has a recombination rate sufficient to give rise to an identifiable genome rearrangement at a base rate of at least about $1 \times 10^{-11}$ occurrences per cell per generation and in a preferred embodiment at a base rate of $1 \times 10^{-4}$. This mammal carrying the selected repeated genetic element is then exposed to a potential carcinogenic agent. Within a relatively short period of time after such exposure, the extent of such genome rearrangement leading to deletion recombination events (DEL) in the mammals is determined as compared to control mammals carrying the repeated element which were not exposed. The exposed mammals can be adults and the determination can be made in the adults by appropriate selection of the repetitive genetic elements. In an embodiment the genome rearrangement is identified by a change in phenotypic expression associated with the genome rearrangement or alternatively identified by PCR analysis of the DNA sequence directly.

In an embodiment, a duplication of 7.0 kb of exons 2 and 3 of the Hprt gene is constructed and used as the DEL substrate in the transgenic mouse. The construction of the duplication and insertion and testing in murine embryonic stem cells (ES) cells is described in the Examples herein below. When the construct is integrated into the Hprt wildtype locus there is a disruption duplication of the Hprt gene which is the DEL Substrate/Construct and which renders the Hprt gene nonfunctional. These Hprt– cells revert to the Hprt+ wildtype by a deletion recombination event (DEL).

The following is a list of terms used in this application. These terms are terms of art and are defined in general as known in the art. In addition, applicant's co-pending application, U.S. Ser. No. 08/266,014 filed Jun. 27, 1994, now U.S. Pat. No. 5,762,908 provides full definitions of the terms and these definitions are incorporated herein by reference. Further, many of these terms are also used in applicant's U.S. Pat. No. 4,997,757, the entire disclosure of which is hereby incorporated by reference into this specification. Definitions of the terms are also found in Goodenough's "Genetics," Third Edition (Saunders College Publishing, New York, 1984), in John M. Walker et al.'s "The Language of Biotechnology: A Dictionary of Terms" (American Chemical Society, Washington, D.C., 1988), and in a text by W. Ralph Singleton entitled "Elementary Genetics", Second Edition (American Book Company, New York, 1962), and are also defined in a book by Benjamin Lewin entitled "Genes IV" published by Oxford University Press, New York, N.Y. Additionally many of the terms used in this specification are also defined in a book by James D. Watson et al. entitled "Recombinant DNA" published by Scientific American Books, New York, N.Y. These texts are incorporated herein in by reference. The terms are: allele, DNA repair enzymes, repetitive genetic element (also referred to as duplications), phenotype, genotype, phenotypic expression, genome rearrangement, genetic endpoint, genotoxic substances, DNA, coding region, crossing over, homologs, gene, translocations, gene amplification, insertions and rearrangements within genes, deletions., intrachromosomal recombination, interchromosomal recombination, homology, mutation, plasmid, restriction enzyme, sequence homology, mutagenesis, PCR and wild type.

Briefly, the term genetic endpoint generally refers to the secondary effect of genotoxic substances which interact and change DNA.

Briefly, the phenotype is the observable expression of the genotype. Coat color, eye color, enzyme activity are examples of phenotypes. Changes in phenotypic expression reflect changes in the genotype.

Briefly, the term "Genome rearrangement" is another genetic endpoint. A genome is a complete haploid set of chromosomes. A diploid organism has two sets of chromosomes. A genome rearrangement is any genetic event that rearranges the order of genes within a haploid genome or between a haploid genome and other genetic elements, thereby creating a new environment for particular genes either on a different chromosome or on the same chromosome in a different position. Briefly, the term repetitive genetic element refers to a duplication of a portion of the genomic DNA sequence that is either in tandem or separated by a non-duplicated sequence and which will pair to allow intrachromosomal or interchromosomal crossing over.

The repeated genetic elements can be those identified in the genome due to naturally-occurring events or alternatively they can be engineered using techniques in developing transgenic mice that are known in the art and described herein. The repetitive genetic elements are selected so as to allow identification of the recombination events in the exposed animal and in any appropriate tissue or cellular sample.

As is known to those skilled in the art, about 25 percent of the human genome is made up of repetitive DNA sequences which may be either tandem repeats or interspersed repetitive elements. In the human genome recombination events between these repetitive genetic elements occurs at a rate sufficient to give rise to an identified genome rearrangement at a rate of at least about $1 \times 10^{-11}$ occurrences per cell per generation under ambient conditions (See Schmid et al, 1989).

Various families and subfamilies of repetitive elements have been identified in the human genome, such as Alu family repeats consisting of short interspersed repeats (Jelinek et al., 1982), the KpnI family of long interspersed element repeats (Singer, 1982), transposon-like Human Elements (THE-1 sequences) which belong to the family of retrotransposons (Paulson et al., 1985), Long Terminal Repeat (LTR) sequences consisting of short, repetitive elements (Paulson et al., 1985), Long Interspersed Elements (LINE sequences) (Singer, 1982), etc.

Because of the large number of repetitive sequences scattered throughout the human genome, intrachromosomal recombination events between direct repeats may occur widely in the genome (see, e.g. Calabretta et al, 1982) and may lead to various genetic disorders if an essential locus is deleted or disrupted during the process. In fact, various genomic rearrangement events involving deletions have been associated with different abnormalities such as Ataxia telangiectasia (AT), Prader-Willi Syndrome (PWS), Angelman Syndrome (AS), etc. A considerable portion of the human genome is made up of non-essential DNA sequences or intron regions and deletion events occurring in these regions may go unnoticed in the majority of cases, when not directly linked to a disorder phenotype. However, such loci may serve as useful markers for monitoring deletion recombination events occurring in the genome.

It is well-known that the human genome is similar to all other mammalian genomes inasmuch as all such mammalian genomes are made up of a substantial number of repetitive DNA sequences which may be either tandem repeats or interspersed repetitive elements and, thus, in these mammalian genomes, recombination occurs at a rate sufficient to give rise to an identifiable genome rearrangement at a rate of at least about $1 \times 10^{-11}$ occurrences per cell per generation under-ambient (normal) conditions. Although the nature of the repetitive DNA sequences may vary from one mammalian genome to another, all of such mammalian genomes contain a sufficient number of families of repetitive DNA sequences which contain members that are sufficiently homologous to recombine with each other at a rate sufficient to give rise to an identifiable genome rearrangement at a rate of at least about $1 \times 10^{-11}$ occurrences per cell per generation under ambient conditions.

Thus, as will be readily apparent to those skilled in the art, one may use rodents such as mice and/or rats and/or guinea pigs and/or rabbits and/or hamsters, and/or monkeys and/or human beings, and the like as a source for the repetitive genetic elements and as an organisms in which genomic rearrangement of these elements may be measured.

Several such mammals are commercially available. One such mouse is sold by the Jackson Laboratory of 600 Main Street, Bar Harbor, Me. 04609 as product number C57BL/6J-p"'. This mouse, which is known as pink-eye unstable, is listed on page 5.60 in Catalog "Handbook on Genetically Standardized Jax Mice" number S7/82, which was published by Jackson Laboratory in July 1982. This mouse is described in the "Jax Mice" price list published by the Jackson Laboratory on July 1988 as stock No. JR0028. It is also described in the "List of mutations and mutant stocks of the mouse" also published by the Jackson Laboratory in July 1988. A general description of this mutation and other mutations useful in applicants process can be found e.g. in a book by W. K. Silvers entitled "The coat colors of mice" published by Springer Verlag, New York (1979). This mouse is the subject of the invention in applicant's co-pending application, U.S. Ser. No. 08/266,014 filed Jun. 27, 1994 and incorporated herein by reference.

Another such mouse which may be used in the process of this invention is also commercially available from the Jackson Laboratory. This latter mouse is sold by the Jackson Laboratory as Product numbers DBA/1LacJ, DBA/1J, and DBA/2J, each of which contain the mutant allele. It is known as dilute (d') coat-color mutant DBA mouse and is listed on pages 17 and 18 in Catalog "Handbook on Genetically Standardized Jax Mice" fourth edition, which was published by Jackson Laboratory in April 1991. This mouse is listed in the "Jax Mice" price list on page 7 published by the Jackson Laboratory on July 1988 as strains DBA/1J, DBA/1LacJ and DBA/2J. A general description of this mutation can be found e.g. in the aforementioned book by W. K. Silvers entitled "The coat colors of mice". This dilute (d') coat-color mutant DBA mouse has been described by Copeland et al. (1983), and Seperak et al. (1988).

As described herein above, these mutations have a limited tissue range of expression. Therefore, additional models are needed.

A transgenic mammal provides a means of engineering mammals carrying the appropriate repetitive genetic elements (DEL Construct) in their haploid genome. The repetitive genetic elements (DEL construct) contained in the haploid genome of the mammal are selected to be sufficiently homologous so that, under ambient conditions, and without intentionally exposing the mammal to any suspected carcinogen, the repetitive genetic elements recombine with a frequency of recombination at a rate sufficient to give rise to an identifiable genome rearrangement (deletion event; DEL) at a rate of at least about $1 \times 10^{-11}$ occurrences per cell per generation under ambient conditions. The repetitive genetic elements for use in engineering mammals can be selected from naturally occurring repetitive elements as described herein below or alternatively genetic engineering techniques can be used to engineer a duplication of an element thereby creating a repetitive genetic element.

In a first embodiment the beta-lactamase gene (lacZ) that is commonly used as a marker gene in genetics (e.g. Brenner et al. 1989, Zakany et al. 1990, Biard et al. 1992) is used. This gene takes part in metabolism of lactose in E. coli. Enzymatic activity of the lacZ gene can be detected as blue color after incubation with X-gal. The intensity of the blue color is directly proportional to the gene activity. The lacZ gene is frequently used as a transgenic marker facilitating evaluation of gene expression on the cellular level in tissues (Brenner et al. 1989, Zakany et al. 1990).

In a second embodiment the Hprt gene is used as the selectable marker in transgenic applications (e.g. Deotschman et al. 1988; Thomas and Capecchi 1987). It has been previously shown that deletion events from two copies of a duplication of the Hprt gene are inducible after treatment with X-rays and alkylating agents in CHO cells (Zhang and Jensen 1992). Recently, applicant has shown that the frequency of DEL recombination in a human cell-line containing a spontaneously arisen duplication of a region of Hprt can be increased after treatment with Salmonella assay positive as well as with Salmonella assay negative carcinogens (see Examples). A DEL construct based on an Hprt duplication has the advantage that the Hprt gene is stably expressed in all tissues, has a defined location on the X chromosome and its genetic and metabolic properties are very well documented. The Hprt gene is well characterized, its protein catalyzes the transfer of phosphorylated ribose to the bases hypoxanthine and guanine in the purine salvage pathway. The Hprt gene is X-linked and thus in cells derived from males there is only one copy making it a suitable system for selection for mutations. Thus, it has been studied extensively in mutation and reversion studies in mammalian cells (Stout and Caskey 1985). In addition, positive selection schemes for the wildtype as well as for the mutant are available in tissue culture. While the loss of the Hprt gene in humans results in Lesch-Nyhan disease, it is not an essential gene and mice with an Hprt mutation do not show the disease (Kuehn et al. 1987).

Many DEL construct-types are useful in the present invention. One of the aforementioned DEL constructs includes a duplication of the mouse Hprt gene including one novel splice site without any bacterial or other vector sequence providing another advantage of the Hprt duplication system.

The transgenic parental strains, and where appropriate as well as for knockout models, are constructed using standard methods known in the art and as set forth in U.S. Pat. Nos. 5,614,396 5,487,992, 5,464,764, 5,387,742, 5,360,735, 5,347,075, 5,298,422, 5,288,846, 5,221,778, 5,175,385, 5,175,384, 5,175,383, 4,873,191, 4,736,866 as well as Burke and Olson (1991), Capecchi (1989), Davies et al. (1992), Dickinson et al. (1993), Duff and Lincoln (1995), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

More specifically, any techniques known in the art may be used to introduce the repetitive genetic elements expressibly into animals to produce the parental lines of animals. Such techniques include, but are not limited to, pronuclear microinjection (U.S. Pat. No. 4,873,191); retrovirus mediated gene transfer into germ lines [Van der Putten et al., 1985]; gene targeting in embryonic stem cells [Thompson et al., 1989 and U.S. Pat. No. 5,614,396]; electroporation of embryos [Lo, 1983]; and sperm-mediated gene transfer [Lavitrano et al., 1989]. For a review of such techniques see Gordon [1989]. As appropriate, cells and tissues from the animals may be isolated for cell culture as is known in the art.

Further, the transgenic strain of the present invention in addition to carrying an endogenous repetitive genetic element transgene may also carry an additional transgene. For example, as discussed herein above the compound which is being tested may not be directly carcinogenic, rather metabolism of the compound generates carcinogenic metabolites as described herein above for humans. Therefore, it will be useful in constructing the transgenic mammal to also include in addition to the repetitive genetic elements, the appropriate human genes for metabolizing the class of compounds being tested. In addition, to direct insertion of the human transgene into the mammal with or without the endogenous gene knocked-out, the endogenous gene may be mutated using gene targeting to the human sequence. That is, the endogenous gene for metabolizing the compound has been "humanized" and/or mutated (Reaume et al, 1996) so that a test system more representative of humans is provided. It should be noted that if the animal and human sequence are essentially homologous a "humanized" gene is not required. Further, a mammal such as the $p^{un}$ mouse described herein could also be engineered to carry an appropriate human or humanized gene for metabolizing a potential carcinogen.

Those skilled in the art are aware of how to determine whether repeated genetic elements exist in the genome of a mammal and which will lead to an identifiable genome rearrangement. First, an indication of the presence of repeated elements in the genome is the fact that they recombine with each other to give rise to genome rearrangements. Genome rearrangements can, for instance, give rise to reversion of a mutation, such as, in the case of the aforementioned C57BL/6J-$p^{un}$ as well as the DBA mice. One characteristic of the reversion events that occur by genome rearrangement may be that they occur at a higher rate than regular reversion events that occur by mutation. Regular germ line mutation events occur about 6.7 times in ten million ($0.67 \times 10^{-6}$) gametes, (see e.g. Schlager and Dickie (1967). The aforementioned $p^{un}$ mutation reverts at a rate of 6.8 times in ($0.68 \times 10^{-3}$) 10,000 gametes, see Melvold, (1971). Thus, the $p^{un}$ mutation shows a 1000 fold higher germ line reversion rate, by genome rearrangement, compared to other mutation rates. Similarly, the second aforementioned mutation, $d^v$ in DBA mice shows a reversion rate of $3.9 \times 10^{-6}$ events per gamete, again at least a five fold higher rate than other recessive mutation alleles show (see Seperack et al, 1988). The reversion of the $d^v$ allele is also due to genome rearrangement, (see Copeland et al, 1983). This is also true for somatic reversion rates. Somatic reversions occur in the somatic cells of the animal rather than in the germline. Thus somatic reversion events can be detected in the same animal rather than in its offspring, similarly as for germ line mutations. As disclosed above, the $p^{un}$ allele reverts spontaneously in about 3.8% of the animals and the $d^v$ allele reverts in about one per one million animals, (see Seperack et al., 1988).

As known to those skilled in the art, genome rearrangements and repeated elements can be detected by Southern blotting (Copeland et al, 1983). Southern blotting has been used to determine that the reversion of the $d^v$ mutation occurs by homologous recombination involving the viral LTRs, which results in one form of genome rearrangement. The method of Southern blotting is well known to those skilled in the art and may be found e.g. on pages 127 to 133 in a book by Watson et al. entitled "Recombinant DNA" published by Scientific American Books, W. H. Freeman and Company, New York in 1992. In one example, of this technique it is expected that the Southern blot of DNA isolated before the genome rearrangement happened will show two fragments, indicating the repeated genetic elements. In that case, DNA isolated from cells after the genome rearrangement happened digested with the same restriction enzymes and hybridized to the same fragment should show only one fragment.

If the fragment that is repeated to form the repeated elements is not known, genome scanning may be used to find the repeated elements. An example of this type of determination is the analysis of the $p^{un}$ mutation (Brilliant et al., 1991). The study demonstrated that the duplication was at least 17.8 kilobase pairs of DNA and that reversion to the wildtype p allele is due to a deletion of one copy of the repeated element. This shows the advantage of using a model system that detects a genome rearrangement simply by the presence of a change in the phenotype of the test animal.

The genome scanning technique is similar to the DNA fingerprinting technique of Jeffreys et al. (1985) and is based on the aforementioned Southern blotting technique. The difference in the DNA fingerprinting method is that genome scanning uses a repetitive DNA probe of much higher copy number of about 1000 copies per genome, as compared to about 60 per genome for DNA fingerprinting. Therefore, a larger fraction of the genome can be scanned for sequence differences (such as repeated elements). However, without limitation, both techniques may be used to determine the presence of repeated elements.

The restriction fragment length polymorphism (RFLP) technique, another variation of the Southern blotting technique, can also be used to determine the presence of repeated elements. Those skilled in the art are familiar with the RFLP technique, that is for instance described on pages 525–528 and elsewhere in the aforementioned book by J. D. Watson et al. entitled "Recombinant DNA". With RFLP the DNA of coisogenic mice of wildtype and mutant (presumably containing the repeated elements) are subjected to Southern blots using single copy or multiple copy genetic elements as probes. When a RFLP is detected and its occurrence correlates with the occurrence of the aforementioned mutation then this is an indication for the presence of repeated genetic elements.

The repeated elements may also be detected using the PCR (polymerase chain reaction) technique which is described, e.g., in U.S. Pat. Nos. 4,683,202, 4,683,195, 4,800,195, and 4,965,188. The disclosure of each of these patents is hereby incorporated into this specification.

By way of illustration, to be useful for determination of the presence of repeated genetic elements the oligonucleotide primers used may be designed so that the amplified fragment includes one junction created by the amplification. Thus, the junction created by the amplification is not present in the DNA from the mammals without the amplification or from those mammalian cells which have undergone genome rearrangement. In this case, the absence of said DNA fragment produced by PCR may indicate a genome rearrangement. On the other hand, the primers may be designed so that the PCR amplified fragment is of aberrant size that is only obtained from cells that underwent the genome rearrangement.

Further, repeated genetic elements can be detected by DNA sequencing. Utilizing automated sequence apparatuses for example. In that way repeated genetic elements are defined by at least two homologous sequences in the haploid genome of a mammal. Other methods that can identify repeated genetic elements can also be used to determine whether a particular mammal falls within the scope of this invention.

In the practice of the present invention the genome rearrangements are scored in order to determine the carcinogenicity of the tested compound. Therefore, in addition to having a genome with repeated genetic elements, these will lead to an identifiable genome rearrangement. The mammal either selected or engineered to be used in the process of this invention also exhibits an extraordinarily high frequency of such identifiable genome rearrangement when subjected to a specified carcinogenic agent for a specified period of time.

In the test used to evaluate the genome rearrangement to see if it is suitable for the method of the present invention, the carcinogenic agent used is gamma radiation. In the test, the mammals to be evaluated are subjected to a dose of 400 rads ("iradiation absorbed doses") per mouse. Thereafter, from about 0 to about 30 days after such irradiation, the mammals are evaluated by conventional means as described herein below to determine whether an identifiable genome rearrangement has occurred. Those animals which have an identifiable genome rearrangement under the conditions of this test at a rate of at least about 1 in 1,000,000 animals tested and, preferably, at least about 1 in 1,000 animals tested are preferred for the method of the present invention. It is more preferred that the identifiable genome rearrangement occur in at least once in each 500 animals tested.

In some cases, with radiation sensitive animals, the mammals will die as a result of the radiation prior to the 30 days waiting period. These radiation sensitive mammals are suitable for use in applicant's process.

Those skilled in the art know how to determine the existence of an identifiable genome rearrangement. Thus, for example, with the pink-eye unstable mouse ($p^{un}$), and/or the DBA mouse, one may count the number of mice whose coats contain patches of changed coat color. These mutations show a lighter, more dilute color than the wild-type mice (see Melvold, 1971 and Copeland et al., 1983). Dark patches on the dilute fur will indicate genome rearrangements that occurred at some time during the development of the embryo. The derivative cells from that genome rearrangement divide and give rise to one patch of wild-type color on the fur of the animal. The patches are most easily detected 12 to 14 days after birth because the fur coats of the mice have not yet been fully formed. To record the results pictures of the animals can be taken. Alternatively, the patches can be detected under the microscope. In this way, even single hairs can be evaluated. Similar methodology has been used in the aforementioned "mouse spot test" and has been disclosed, for instance, in an article by Searle and Stephenson(1982). For this purpose the animal may be sacrificed and its skin removed. Samples of the fur may be prepared to allow examination under the microscope. In this way, many fewer animals have to be examined, since one can count many more (microscopically small) effects of genome rearrangements in one mouse.

By way of illustration, one may also determine the rate of genome rearrangement by Southern blotting technique. For instance, a fragment of the amplified region may be used as described in the aforementioned article by Brilliant et al (1991). Without limitation, the genome rearrangement may be detectable by a change in the intensity of the hybridizing band in the Southern blot. Furthermore, the genome rearrangement may be detectable by the appearance (or disappearance) of a certain fragment in the Southern blot.

Thus, by way of further illustration, one may also determine the rate of genome rearrangement by the PCR technique. Without limitation, the primers may be designed so that the PCR amplified fragment has a novel size that is only obtained from cells that underwent the genome rearrangement. Since PCR is an extremely sensitive method for the detection of certain amplified fragments, this method can, for instance, be used with different tissues of a single mouse. A single mouse or several mice are sacrificed and different tissues and DNA isolated from these tissues.

Quantitative PCR can also be employed. For this purpose a set of standard primers can be used as controls in multiples of the same reaction. The first set of primers amplifies a sequence common in the DNA of a first mouse, that will be tested for the amount of genome rearrangement in its DNA. This control is simply used to verify that PCR works with the isolated DNA and the chosen conditions.

A second set of primers only amplifies a fragment from the cloned DNA construct after rearrangement from the DNA of a second mouse that has the desired rearrangement in its DNA but not from the DNA of the first mouse. The concentration of DNA from the first mouse at which a fragment that is characteristic for the presence of the genome rearrangement will be recorded. This concentration will be compared to the concentration of DNA from the second mouse required to be added to obtain an amplified fragment. The amount of rearranged DNA from the first mouse should be roughly equal to the amount of DNA from the second mouse that was necessary to be added. In this way roughly the ratio of rearranged to unrearranged DNA from the first mouse and the effects of the carcinogens can be determined.

In situ hybridization can also be used to determine the extent of genome rearrangement. For instance, the rearranged gene could be expressed from a strong promoter to be transcribed into a certain species of messenger RNA that is not transcribed in unrearranged cells. Methods for in situ hybridization are well known to those skilled in the art and can be found e.g. on pages 539 to 550 in a book by M. M. Gottesman entitled "Molecular Genetics of mammalian cells" published in Methods in Enzymology volume 151 (1987) by Academic Press, Boston. With in situ hybridization the exact location in different tissues of cells with genome rearrangements can be determined.

Furthermore, one may utilize in situ antibody staining, in which antibodies are caused to interact only with the gene product of those cells which undergo genome rearrangement. This technique is well known to those skilled in the art and is described, e.g., in U.S. Pat. No. 4,968,633, the entire disclosure of which is hereby incorporated by reference into this specification.

By way of further illustration, the chloramphenicol acetyltransferase (CAT) gene could be used to determine the extent of genome rearrangement. As known to those skilled in the art sensitive enzymatic assays for CAT activity exist as described e.g. on pages 382 to 397 in the aforementioned book by M. M. Gottesman entitled "Molecular genetics of mammalian cells". A transgenic mammal is used for this experiment that contains a construct in which the CAT gene is present in two incomplete parts with overlapping homology or in which the CAT gene is removed from its promoter. In whatever way the construct is designed, the CAT gene should only be expressed after the genome rearrangement occurred. The cells from different tissues of the mammal can be disrupted by sonication or by cycles of freeze-thawing and the cellular debris should be removed by centrifugation. Thereafter CAT activity can be determined from the supernatant. The amount of CAT activity should be proportional to the amount of cells having undergone genome rearrangement.

The lacZ gene of *Escherichia coli* encodes beta-galactosidase. As known to those skilled in the art the lacZ gene is used for many purposes in molecular biology to study gene expression. The expression of the lacZ gene can be determined, for instance, by the white to blue color method. This method relies on the fact that 5-Bromo-4-chloro-3-indolyl-beta-D-galactopyranoside (known as X-GAL) changes in color from colorless to dark blue when incubated with beta-galactosidase, the product of the lacZ gene. Use of the lacZ gene in molecular biology can, for instance, be found in the aforementioned book by J. D. Watson. X-GAL is commercially available from many sources, for instance, from Sigma Chemical Company of St. Louis, Mo. Since X-GAL readily diffuses through membranes and is not toxic, it can be used to detect those cells that express the lacZ gene, they turn blue. It has also been shown that it can be used in mammalian cells to identify those cells that express the lacZ gene (Brenner et al, 1989). Thus, the lacZ gene could be used in applicant's process. A transgenic mammal is used for this experiment that contains a construct in which the lacZ gene is present in two incomplete parts with overlapping homology or in which the lacZ gene is removed from its promoter. In whatever way the construct is designed, the lacZ gene should only be expressed after the genome rearrangement occurred. After the mice are sacrificed they can either be dissected or they can be mounted and thin sections can be sliced with the proper techniques and equipment. Thus the expression of the lacZ gene can be detected in the cells that underwent rearrangement by a change of the color to blue (Zakany et al, 1990).

Without limitation, another way to detect the occurrence of genome rearrangements is by fluorescence-activated cell sorting (FACS). This technique is well known to those skilled in the art and is for instance disclosed in the aforementioned book by M. M. Gottesman entitled "Molecular Genetics of mammalian cells" published in Methods in Enzymology volume 151 (1987) by Academic Press, Boston. The principle of this method lies in the fact that cells that emit fluorescent light can be counted in a FACS machine. Antibodies can be isolated against a product which is expressed only in those cells that underwent genome rearrangement.

For instance,. antibodies directed against the beta-galactosidase are available (the product of the aforementioned lacZ gene) and the aforementioned animal with a lacZ construct may be useful for this purpose (Nolan et al, 1988). The antibody is conjugated to a fluorescence emitting dye, so that, when the antibody binds to the cells that underwent genome rearrangement those cells start to emit fluorescence. The animal containing said lacZ construct can be sacrificed, different tissues can be isolated and the cells obtained. These cells can be incubated with the antibody that only labels those cells that underwent genome rearrangement. Thereafter, the cells that underwent genome rearrangement can be counted in a FACS.

By way of further illustration, one may use in situ PCR (polymerase chain reaction) to quantify the frequency of genome rearrangement within the genome of a mammal. As is known to those skilled in the art, in situ PCR is used to amplify nucleic acids that hybridize to the primers used in the reaction so that amplification will only occur within those cells in which genome rearrangement occurred. See, e.g., U.S. Pat. Nos. 5,021,335 and 5,028,525, the disclosures of which are hereby incorporated by reference into this specification.

The above discussion provides a factual basis for the use of transgenic animals constructed to carry a repetitive genetic element for use in DEL assays to determine carcinogenic potential of a compound. The methods used with and the utility of the present invention can be shown by the following non-limiting examples and accompanying figures.

EXAMPLES

General Methods

General Methods in Molecular Biology

Standard molecular biology techniques known in the art and not specifically described were generally followed as in Sambrook et al., *Molecular Cloning: A Laboratory Manual*, Cold Springs Harbor Laboratory, New York (1989), and in Ausubel et al., *Current Protocols in Molecular Biology*, John Wiley and Sons, Baltimore, Md. (1989) and in Perbal, *A Practical Guide to Molecular Cloning*, John Wiley &

Sons, New York (1988), and in Watson et al., *Recombinant DNA*, Scientific American Books, New York. Polymerase chain reaction (PCR) was carried out generally as in *PCR Protocols: A Guide To Methods And Applications*, Academic Press, San Diego, Calif. (1990).

Example 1

Summary of Previous Examples in Co-Pending Applications and Patents

Assays for Deletions in Yeast, Human Cells and in vivo in Mice

Applicant has previously constructed and/or used intrachromosomal recombination assays scoring for deletion events between repeated his3 deletion alleles in the yeast *Saccharomyces cerevisiae* (Schiestl 1989; Schiestl et al. 1989; Carls and Schiestl 1993; Brennan et al. 1994) between sequences of an internal duplication of exons 2 and 3 of the Hprt gene in a human lymphoblastoma cell line (see herein below) and between the two deletion alleles of the p gene, $p^{un}$ (for p unstable) in the mouse (Schiestl et al. 1994). It was found that intrachromosomal recombination events resulting in deletions (DEL events) in yeast occur more frequently after treatment with Salmonella-assay-positive as well as Salmonella-assay-negative carcinogens (Schiestl 1989). In the same way, DEL recombination events in human cells are inducible by both kinds of carcinogens (Aubrecht et al., 1995; see herein).

To determine whether deletion events between two alleles of a gene duplication are inducible in vivo in a mammal the pink-eyed unstable, ($p^{un}$) mutation in the mouse has been used (Schiestl et al, 1994 and co-pending application). The $p^{un}$ mutation causes a dilution of the pigment in coat-color and eye color and is due to a deletion disruption of the pink-eyed dilute locus creating a DNA sequence duplication of about 75 kb which is a head to tail duplication (Brilliant et al. 1991, Gondo et al. 1993). Reversion of this mutation is easily scorable as black spots on the dilute coat and is due to a deletion of one copy of the duplicated sequence (FIG. 1) resulting in production of wildtype melanin in melanocytes. The frequency of reversion of the $p^{un}$ mutation is uniquely sensitive towards the effects of x-rays. $p^{un}$ reversion events are also inducible by the Salmonella-assay-positive carcinogens EMS, MMS, ENU and benzo(a)pyrene as well as with the Salmonella-assay-negative carcinogens trichloroethylene, benzene and sodium arsenate (see below). Most of these same chemicals are positive in the yeast DEL assay (Schiestl 1989; Carls and Schiestl 1993) and those that have been tested are also positive in the human cell culture DEL assay (see herein below). These results are important for a higher confidence in the comparison for in vitro versus in vivo results with the DEL assay. In addition, there is an excellent correlation between the carcinogenic activity and the effects of these chemicals on the frequency of deletions.

The usefulness of DEL assays has also been demonstrated by others. The yeast DEL assay has been adapted to a microtiter plate format and has been validated at Xenometrix Inc. Boulder, Colo. (Sommers et al. 1995). Certain tryptophan photoproducts that increase the frequency of sister chromatid exchanges (SCE) in CHO cells but are negative with the Salmonella assay (Rannug et al. 1992) gave a positive response with the yeast DEL assay. Ethylene oxide induced SCE and chromosomal aberrations in vivo in monkeys but its analog propylene oxide was ineffective. In the Salmonella assay both compounds scored positive to the same extent. However, DEL recombination was 10 fold more inducible with ethylene oxide than with propylene oxide (Agurell et al. 1992). In addition, using a duplication of part of the Hprt gene it has been shown that deletions in CHO cells are inducible by several mutagenic carcinogens (Zhang and Jenssen 1992).

Why do "Nonmutagenic" Carcinogens Induce Deletions?

In an attempt to understand the inducibility of DEL recombination by Salmonella assay negative carcinogens one has to consider the molecular events that are involved in the two assays. The Salmonella assay is based on the induction of point mutations reverting from a histidine auxotroph mutation to wildtype. Some of the Salmonella negative carcinogens that are positive in the DEL assay are clastogens such as urethane, benzene (Heddle 1983). An agent that induces DNA breaks, in particular double-strand breaks, is toxic. The more toxic in relation to its mutagenicity a compound is the less likely it is to be detected by the Salmonella assay. Thus, it has been shown that some direct acting (or Salmonella assay positive) carcinogens induced deletions in yeast in a linear dose response starting at concentrations 100 to 1000 fold below the first dose at which cell toxicity is seen. However, the Ames assay negative carcinogens induced deletions with a threshold and only at doses which caused significant cell killing.

A double strand-break may destroy the mutant his gene but will not lead to the reversion of a point mutation. On the other hand, strand breaks, in particular double-strand breaks, are the most powerful inducers of DEL recombination. A mutation in DNA ligase resulting in a high load of single and double strand breaks in yeast increases DEL recombination about 100 fold (Schiestl and Prakash, 1988). Agents that cause strand breaks like X-rays, MMS (Schiestl et al. 1989) and oxidative mutagens (Brennan and Schiestl 1994) are powerful inducers of DEL recombination but are very weak inducers of reversions in the Salmonella assay. MMS and X-rays are also negative in vivo with the Big Blue™ mouse that also detects mostly point mutations.

How are Current Transgenic Mouse Models Different From the Proposed Model

Early results with a transgenic mouse system scoring mainly for point mutations within lacI marketed as the "Big Blue Mouse™" from Stratagene are partly discouraging because potent carcinogens do not induce mutations in this system. For instance, carbon tetrachloride produces significant increases of replication in the liver with no increase in hepatic mutant frequency (Mirsalis et al. 1993). DEL recombination in yeast is inducible with carbon tetrachloride (Schiestl 1989). Methylmethane sulfonate (MMS) has also been called a radiomimetic agent, because it may lead to double-strand breads upon repair of the alkylated base residue. MMS fails to induce lacI mutations in mice even when administered for up to 21 days (Mirsalis et al. 1992). On the other hand, MMS induced a high frequency of deletion in vivo in the mouse (see below).

One transgenic mouse model exists but it cannot be used to detect DEL recombination events (Murti et al. 1992; 1994). These mice contain two nonfunctional lacZ genes under the regulatory control of a spermatogenesis-specific promoter. The two defective lacZ alleles can undergo intrachromosomal gene conversion to produce a wildtype lac+ copy that can be identified. It has been shown that chlorambucil increased the frequency of conversion events. There are many differences between this model and the ones described in this proposal. First a spermatogenesis-specific promoter has been used so that tissue specific effects cannot be detected (Murti et al. 1994). Secondly, the spontaneous frequency is rather high (about 2%) which may be due to the high frequency of homologous meiotic recombination but may make the detection of mutagen induced recombination above this level difficult. This can be compared to a frequency of about $10^{-4}$ to $10^{-5}$ of spontaneous reversion events of DEL recombination in most systems (Zhang and Jenssen 1992; see herein below) including the in vivo mouse system (Schiestl et al. 1994). In the third place, in the Murti et al. (1992) model the construct can only revert by intrachromosomal gene conversion but not by deletions. In contrast, in the transgenic animals of the present invention the constructs can only revert by deletion but not by intrachromosomal gene conversion. Applicant and others have previously shown that most of the Salmonella assay negative carcinogens are also negative for the induction of gene conversion (Schiestl 1989; Schiestl et al. 1989 and references cited therein). Thus, the present invention detects a different genetic event than the Murti et al. (1994) assay.

The Yeast DEL Assay

A plasmid with an internal fragment of the HIS3 gene has been integrated at the HIS3 locus yielding an integrative disruption of the HIS3 gene. This resulted in two copies of the HIS3 gene each having one terminal deletion. This construct reverts to HIS3+ by recombination of the two his3 deletion alleles which is in 99% of the cases associated with deletion of 6 kilobasepairs of DNA which comprises the entire integrated plasmid. Thus, this system has been termed deletion (DEL) assay.

DEL recombination is under different genetic control than interchromosomal recombination (ICR) or meiotic recombination (Schiestl and Prakash 1988; 1990). These data suggest that the mechanism of DEL recombination differs from that of interchromosomal recombination and meiotic recombination. Therefore, DEL recombination seems to occur by a different mechanism than interchromosomal recombination and thus may show a different pattern of inducibility. It was found that DEL recombination is inducible with a variety of Salmonella assay negative carcinogens that are not detectable with the Ames assay or with other short-term tests (Schiestl 1989; Schiestl et al. 1989). Carcinogens that are detectable with the Salmonella Assay, namely UV and γ irradiation, MMS, EMS, 4-NQO, Nitrogen mustard, Epichlorohydrine, aflatoxin B1, ethylene dibromide, dimethylhydrazine, cyclophosphamide, formaldehyde as well as carcinogens that are not detectable with the Salmonella Assay, namely safrole, ethionine, urethane, auramine, methylene chloride, carbon tetrachloride, cadmium chloride, cadmium sulfate, aniline, 3-aminotriazole, acetamide, thioacetamide, thiourea, DDE, ethylenethiourea, arsenate, benzene, o-toluidine, hexamethylphosphoramide, acrylonitrile, polychlorinated biphenyls all induced DEL recombination. Five mutagenic noncarcinogens have been used: hydroxylamine hydrochloride sodium azide, 5-bromouracil and 2-aminoantipurine. Three of these five false negatives with the Salmonella assay do not induce deltions in yeast. Four Ames Assay negative carcinogens, TPA, diethylhexylphthalate, phenobarbital and diethylstilbestrol, also gave negative results with the DEL assay. These data show that 12 Salmonella assay positive carcinogens and 21 Salmonella assay negative carcinogens induced DEL recombination (Schiestl et al 1989, Carls and Schiestl 1993, Brennan et al. 1994).

In yeast cells arrested in the G2 stage of the cell cycle, Salmonella assay negative carcinogens showed the same magnitude of induction of intrachromosomal recombination (100 fold) as Salmonella assay positive carcinogens. Mutagenic carcinogens caused an almost linear dose response for induction of intrachromosomal recombination starting at a dose 1000 fold below the lowest toxic dose. In contrast, Salmonella assay negative carcinogens showed a sharp threshold below which no effect was detected, and the first effective dose was always the first toxic dose (Galli and Schiestl, 1995). These results are in agreement with the concept that Salmonella assay negative carcinogens act in an indirect way only at high doses and that exposure to low doses may not cause any significant risk. Carcinogenicity studies are done at the maximum tolerated dose which may be the reason for detection of the Salmonella assay negative carcinogens. For some Salmonella assay negative carcinogens only relatively high doses showed an effect. However, osmotic stress does not induce DEL recombination, since certain sugars like sorbitol and glucose at more than 20% did not induce DEL recombination. The induction is also not an effect of mere toxicity, since very high cell killing (to 0.01% survival) by noncarcinogenic mutagens like sodium azide and hydroxylamine hydrochloride did not increase the frequency of DEL recombination (Galli and Schiestl, 1995).

The particular lesion initiating DEL recombination has also been studied. Preliminary results indicate that DEL recombination is very well induced by single or double-stranded DNA breaks (Galli and Schiestl, 1995). This observation is also supported by the fact that agents producing DNA breakage such as X-rays, MMS, oxidative mutagens (Brennan et al. 1994) and Salmonella assay negative carcinogens that are clastogenic such as urethane and benzene are positive in the yeast DEL assay.

Inducibility of Intrachromosomal Recombination in Mammalian Cells

The next stage was to develop intrachromosomal recombination systems in mammalian cells and in vivo in the mouse and to study their inducibility with carcinogens. Applicant was able to show that intrachromosomal recombination is inducible by carcinogens in human cells (Aubrecht, et al, 1995). A human cell line GM6804 was used. This cell line is derived from a male Lesch-Nyhan patient and consists of Epstein Barr Virus-transformed lymphoblasts. These cells contain a 13.7 kb duplication of a region containing the exons 2 and 3 within the hypoxanthine phosphoribosyl transferase (Hprt) gene (Monnat et al., 1992). The duplicated sequence is a spontaneously arisen substrate for DEL recombination. While this gene is transcribed into mRNA, of a larger size than wild-type Hprt mRNA, a functional protein is not made. It has been shown that this duplication is genetically unstable and that a functional protein can be produced upon intrachromosomal recombination resulting in the wild-type phenotype (Yang et al., 1988). Applicant found that reversion events were induced by exposure to both Salmonella assay positive carcinogens namely UV, X-rays and MMS and Salmonella assay negative carcinogens namely Aroclor 1221, thiourea, benzene and trichloroethylene.

Reversion of the $p^{un}$ Mutation in the Mouse

To determine whether deletion events between two alleles of a gene duplication are inducible in vivo in mammals in response to carcinogens/mutagens the pink-eyed unstable, ($p^{un}$) mutation in the mouse was used as set forth in the co-pending application. The $p^{un}$ mutation is a deletion disruption of the pink-eyed dilute locus creating a DNA sequence duplication of about 70 kb which is a head to tail duplication (Brilliant et al. 1991, Gondo et al 1993). Reversion of $p^{un}$ is due to a deletion of one copy of the duplicated sequence (FIG. 1) resulting in production of wildtype melanin in melanocytes.

Briefly, mice homozygous for pink-eyed dilution unstable C57BL/6J $p^{un}/p^{un}$ obtained from the Jackson laboratory were used in the experiments. An increase in reversion events would give rise to an increase in the number of offspring showing dark patches. The protocol used for this test is similar to the "mouse spot test" (for reviews see Russell et al. 1981; Styles and Penman 1985) that consists of exposing populations of embryonic cells that are destined to multiply in relatively fixed configurations, so that a mutation in one of the exposed cells will give rise to a detectable clone. With the $p^{un}$ mice pregnant females were exposed. The major difference in the two tests is that reversion to wildtype phenotype in the present invention study selects for gain of a function due to precise deletion of a disrupting DNA fragment (see FIG. 1), whereas the "mouse spot test" screens for loss of the wildtype function.

X-rays Induces Reversion of the $p^{un}$ Mutation in Mice

X-ray exposure, a carcinogen and mutagen, has been used to test for inducibility of $p^{un}$ reversions. Matings were set up between mice homozygous for $p^{un}$, and pregnancy was timed. Female mice, 8.5, 9.5 and 10.5 days after conception, were irradiated with 1 Gy of X-ray and dark patches on the coat of the offsprings were counted, and their size and distribution recorded. Irradiation at 8.5 days post conception caused neonatal deaths in about 40% of the offspring (Table 1). With irradiation at later stages viability of offspring improved and only about 1% neonatal deaths occurred when irradiation was carried out 10.5 days post conception. Less than 20% of the offspring irradiated at 10.5 days post conception showed gross morphological abnormalities, while irradiation at the earlier stages showed fewer abnormalities similar to previous findings (Russell and Russell 1954).

The data in Table 1 show that 5.6% of 498 control animals spontaneously developed spots. Irradiation of the female mice 8.5 days, 9.5 days and 10.5 days post conception resulted in a four fold increase over the spontaneous frequency of animals that developed spots. These differences are highly significant at $p<<1\times10^{-6}$ using chi-square distribution values.

The Effect of Chemical Carcinogens on $p^{un}$ Reversion

Since it was previously found that Salmonella assay positive as well as Salmonella assay negative (negative in the Salmonella assay) carcinogens induced DEL recombination in the yeast *Saccharomyces cerevisiae* it was an important further step to determine whether such carcinogens also would increase the frequency of $p^{un}$ reversion events in the mouse. Pregnancy was timed as described above and the animals were injected i.p. at the 10.5th day post-conception with different carcinogens dissolved either in saline or in corn oil. Up to 0.2 ml of solution was injected. The control values measured from spontaneous events at the time the animals were exposed to the chemicals is given for groups of chemicals together with the significance values.

The data in Table 2 show a highly significant increase of $p^{un}$ reversion events for each of the carcinogens tested. The doses for the mouse experiments were chosen based on their fetotoxicity in mice that was obtained from the literature and they are in many cases close to the maximum tolerated doses for the fetus. However, at these doses we did not find any toxic effect on the female adult mice except trichloroethylene caused some sedative effects for several hours. It is difficult to compare the effect of the different chemicals since different doses were not used and hence no dose response was obtained. Taking these caveats in mind, and comparing the level of induction with the average size of the surviving litters (a very crude measure of fetotoxicity), ENU and benzo(a)pyrene were most effective and both induced $p^{un}$ reversion events in more than 50% of the offspring mice. It is particularly interesting that the Salmonella assay negative carcinogens trichloroethylene, benzene and sodium arsenate gave significant induction of $p^{un}$ reversion events. These data further support the positive correlation between induction of DEL recombination and carcinogenicity.

Cigarette Smoke Induces $p^{un}$ Reversion

Using the same protocol as described herein above, the effects of exposure of pregnant $p^{un}$ mice to cigarette smoke and cigarette smoke condensate (CSC) on the spotting frequency in the offspring was investigated. Whole body exposures of female mice were conducted with smoke generated by either filtered or unfiltered cigarettes for 4 hours, or mice were given a 15 mg/kg dose of CSC during their 10th day of gestation. Total particulate matter, $CO_2$, concentration and plasma nicotine and cotinine levels were determined to characterize smoke exposure. There was a significant increase in the number of DNA deletions in the embryo as evidenced by spotted offspring in both smoke exposed groups and in the CSC group. These results suggest that embryos are highly sensitive to the genotoxic activity of cigarette smoke following a single exposure of only four hours.

Mechanism of Induced $p^{un}$ Reversion and PCR Detection of Reversion Events

Figure 1:
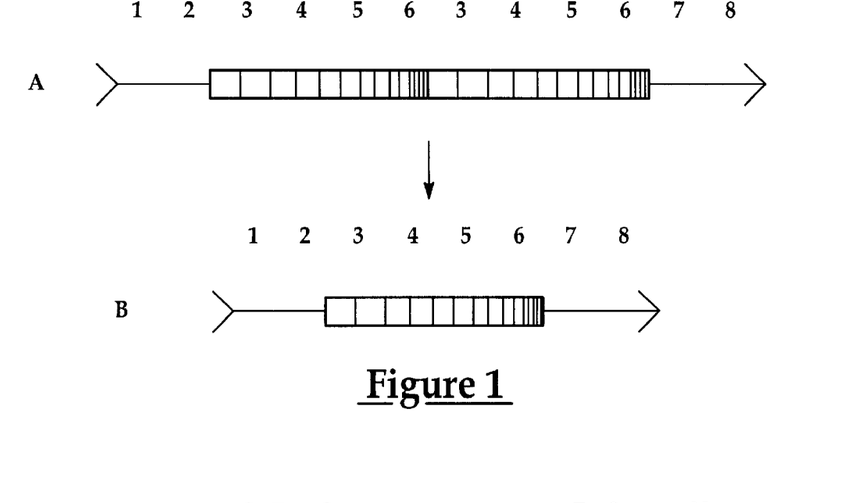
FIGS. 1A–B are schematic diagrams of the structure of the tandem head to tail duplication of the p$^{un}$ mutation and spontaneous reversion event as described and shown in Gondo et al. (1993), the order of linear information in the wildtype (or revertant) being disrupted in the p$^{un}$ duplication (FIG. 1A, numbers above the boxed regions), the reversion event deleting one copy of the duplication and restores the linear information at the p locus (FIG. 1B)

It has been shown that spontaneous reversion of the pun mutation to wildtype is due to intrachromosomal recombination (FIG. 1, Gondo et al. 1993). However, even though unlikely, after irradiation or chemical exposure other different events may occur. These events might include induction of other mutations or turning on genes that could accomplish a similar function (provide a similar phenotype) for example by some sort of bypass suppression. For instance the dsu gene (dilute suppressor) has been shown to suppress the dilute coat color phenotype of mice homozygous for the dilute leaden and ashen mutations (Moore et al. 1990). However, it has been shown that the dsu gene is not able to suppress the phenotype of the p or the $p^{un}$ mutation (Moore et al. 1990). In addition, at least in humans, melanogenesis is inducible by UV light. Firstly, this does not seem to be true with ionizing radiation and it does not seem to apply at least for the spot assay when irradiation has been carried out at the 10th day of embryonic development, before the melanocytes have developed. However, it seems important to determine on a physical basis on the DNA level whether the induced events are due to intrachromosomal recombination.

By genome scanning and molecular cloning techniques, the $p^{un}$ DNA was shown to carry a head to tail tandem duplication of ~75 kilobases, and the loss of one copy of the duplicated DNA was shown to be associated with the reversion phenotype in a spontaneous revertant mouse (Gondo et al., 1993; Gardner et al., 1992). The reversion event occurring in $p^{un}$ mice may be due to a similar mechanism, whereby, one copy of the 75 kb duplicated segment in $p^{un}$ DNA is deleted by an intrachromosomal recombination event. This has been shown by Southern blotting (Gondo et al. 1993) as difference between a revertant mouse strain and the $p^{un}$ mutant. For the molecular detection of reversion events in spots this is not possible. First, the spots are rather small and the chance is very minimal that they will enter the germline. Secondly, because of the small size, Southern blotting is very difficult to carry out if not impossible. PCR also cannot be used for detection on the genomic level since $p^{un}$ contains a tandem duplication and the primers to detect the revertant would have to be placed on each side of the duplication in the unique sequence and it is not possible to amplify a 75 kb piece of DNA. However, it has been shown that in $p^{un}$ animals the p gene is disrupted and contains a 4.8 kb transcript rather than the 3.3 kb transcript of the wildtype or the revertant (Gardner et al. 1992). Since the duplication in p$^{un}$ animals is an internal duplication of the p gene there must be a novel breakpoint within the RNA in the p$^{un}$ transcript versus the revertant or wildtype. These duplication breakpoints have been cloned and sequenced, therefore based on the sequence primers were designed (Schiestly et al, 1997) so that the spots could be analyzed by Reverse Transcriptase-Polymerase Chain Reaction (RT-PCR) for reversion events. These primers amplify a 1.3 kb fragment from p wildtype cDNA while p$^{un}$ transcript results in a 2.6 kb fragment. However, in p$^{un}$ skin sample cDNA the 1.3 kb fragment was found at a ratio of roughly 1:1. This may be due to the fact that about 1 in $10^4$ cells are of the revertant phenotype (Melvold, 1971) and that the shorter 1.3 kb fragment may be preferentially amplified. In fact, in a similar situation in a different experiment using genomic PCR to differentiate a mutated allele from the wildtype in a heterozygous animal, at least four fold more 1.1 kb product than 2.2 kb product was observed. Furthermore, in p$^{un}$ mice the amount of the 4.8 kb transcript is at least 5 fold less than that of the 3.3 kb transcript in p wildtype mice which may be due to decreased expression or mRNA stability (Gardner, 1992).

Black patches as well as gray fur were excised from the same mice and RNA was isolated. In all PCR reactions from cDNA from the black spots from X-ray, EMS, SOA or BEN treated mice the ratio between the wildtype 1.3 kb fragment and the p$^{un}$ 2.6 kb PCR fragment was between 4 to 1 and more than 10 to 1. The presence of some 2.6 kb p$^{un}$ transcript is expected in the spots for at least two reasons. First, there may be contaminating surrounding tissue excised together with the spots. Secondly and most likely, only one of the two alleles of the homozygous p$^{un}$ alleles has recombined to the wildtype p gene leaving the other allele as a p$^{un}$ duplication. In conclusion, the PCR product from cDNA from gray fur contained a ratio of 1:1 of the two species whereas all product from the dark spots contained four to 12 fold more wildtype fragment cDNA.

The presence of p+ transcript expressed in the melanocytes of gray p$^{un}$ mice might be explained by an expected frequency of reversion events of about $10^{-4}$ and the ratio after PCR of 1:1 may be explained by the bias of Taq-based PCR to yield products with under representation of large fragments. In an attempt to avoid this used long range PCR was used. However, a similar result using ELONGASE was obtained which suggests that addition of Pyroccocus speciGB-D thermostable DNA polymerases to PCR mixture did not change the preference of Taq polymerase to shorter DNA fragments.

Example 2

Constructs for Transgenic Animals and Methods of Measurement

The Constructs

All constructs have been designed so that the same constructs can be used on a selective basis in tissue culture or in the transgenic animal. Thus, in the first phase, the constructs are analyzed to establish the spontaneous deletion rates and the inducibility of the deletions by carcinogens. Thereafter, the constructs are used to prepare transgenic animal as described herein above.

LacZ Based Constructs

The first construct to be described makes use of the beta-lactamase gene (lacZ) that is commonly used as a marker gene in genetics (e.g. Brenner et al. 1989, Zakany et al. 1990, Biard et al. 1992). This gene takes part in metabolism of lactose in *E. coli*. Enzymatic activity of the lacZ gene can be detected as blue color after incubation with X-gal. The intensity of the blue color is directly proportional to the gene activity. The lacZ gene is frequently used as a transgenic marker facilitating evaluation of gene expression on the cellular level in tissues (Brenner et al. 1989, Zakany et al. 1990).

A fusion of the lacZ gene with the neomycin phosphotransferase gene is used. The expressed fusion protein has the lacZ activity and can be used as described above. In addition, this fusion protein displays neo activity and confers resistance to G418 (Friedrich and Soriano 1992). The plasmid pGeo was obtained from Dr. Andras Nagy (Mount Sinai Hospital, Univ. of Toronto, ON) and contains the fusion of lacZ with the neomycin phosphotransferase gene and a SV-40 polyadenylation signal driven by a phosphoglucokinase promoter that is ubiquitously expressed (see Nagy et al, 1993). The DEL substrate contains a tandem repeat of one allele of the Geo gene containing a 5-prime deletion and another allele containing a 3-prime deletion sharing about 800 basepairs of homology. The SacI site in pGeo was filled with Klenow polymerase and a NotI linker was inserted resulting in a XhoI NotI fragment containing the 3' portion of the Geo gene lacking its 5' end. The 5' portion of the Geo gene containing a 3' deletion was constructed by replacing the EcoRV site with a NotI site. Both of these Geo alleles were excised as XhoI-NotI fragments and then ligated together into a XhoI site of plasmid pBS with the NotI site between them.

Figure 2:
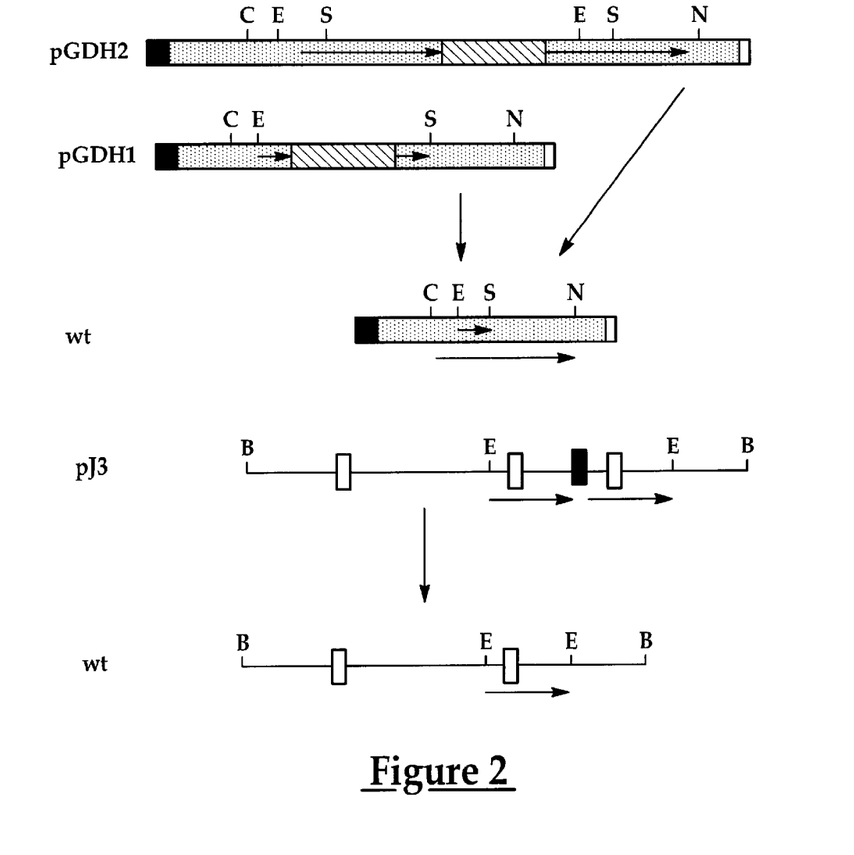
FIG. 2 is a schematic of a DEL recombination substrate.

The resulting plasmid pGD contains a tandem repeat of deletion copies of the fusion genes sharing about 800 bp of homology. Neither of these two fusion genes is intact. As a selection marker placed between these deletion alleles a hygromycin phosphotransferase cassette from pY3 (Blochinger and Diggelmann 1983) containing MOSV (Moloney sarcoma virus) promoter and polyadenylation signal was used. The expression cassette was excised as a PstI-HindIII fragment and blunt-ended with mung-bean nuclease. After addition of NotI linkers this fragment was cloned into the NotI site of pBS and then ligated into NotI of pGD to give the final DEL recombination substrate plasmid pGDH1 (FIG. 2).

In a further embodiment, the Geo alleles in pGDH1 contain about 800 basepairs of homology. This construct is incorporated into cells as described and recombination frequency determined in these cells. For any construct when the spontaneous deletion frequency is below about $10^{-5}$ a construct with more extensive homology may be desirable since it may give a higher spontaneous frequency. Therefore, another construct pGDH2 with more extensive homology is constructed. The pGDH2 recombination substrate contains about 2.9 kb of homology between the two deletion alleles (FIG. 2).

A Hprt duplication containing 2.3 kb of homology reverted about once in $10^5$ cells (Zhang and Jenssen 1992). With this level of deletion events it is possible to detect the spontaneous level with quantitative PCR as described herein above, therefore the lacz system should also have a detectable spontaneous level. Quantitative PCR has for instance been used to determine the number of deletion events in mitochondrial DNA (Cortopassi et al. 1992, Soong et al. 1992). Deletion levels at about $10^{-6}$ in different parts of the brain could be detected (Soong et al. 1992). The 5' truncated allele is cloned by changing the NcoI site into a NotI site. In another copy of the Geo allele in a further embodiment the ClaI site is changed into a NotI site. Both alleles are subcloned into the XhoI site of pBS containing a NotI site between them. Thereafter, the hygromycin phosphotransferase expression cassette is inserted into NotI in the center of the duplication.

The two duplicated Geo alleles of the integrated PGDH plasmids undergo intrachromosomal recombination events resulting in excision of the intervening sequences and restoration of the wild type Geo gene. The product of this gene is traced by the lacZ enzyme reaction, by antibody staining, and can be detected with quantitative PCR. It also can be selected for in tissue culture on medium containing G418 as known in the art.

The staining procedures makes this system suitable to be used as cell lineage marker to trace the contribution of particular cells in the embryo to different tissues. This is because all cells originating from one cell that underwent DEL recombination inherit the deletion event or the wildtype lacZ activity. Thus, deletion events with the appropriate inducer can be induced (e.g. with X-rays) at a particular time in development. Taking about a five fold induced reversion frequency into account (as obtained in preliminary results with the $p^{un}$ reversion system) one may assume that 80% of the events happened in response to, and after, the X-ray treatment. This would make this system useful as cell lineage marker.

Hprt Based Constructs
Construction of a Plasmid Containing Exons 2 and 3 of the Hprt Gene A pUC19 based plasmid (J3) that contained exons 2 and 3 of the Hprt gene was obtained from Dr. Nobuju Meada. The 7.0 kb BamH1 genomic DNA fragment included approximately 1.5 kb of intron 1, the 107 bp exon 2, the 2.8 kb intron 2, the 184 bp exon 3 and approximately 2.4 kb of intron 3. In order to create a genomic duplication of exons 2 and 3, a construct was produced that contained sequences from intron 3 followed by exon 3, the 2.4 kb intron 3 sequence, a 1.6 kb neomycin resistance cassette, the 1.5 kb intron 1 sequence and the rest of intron 2. This plasmid, designated S4, therefore contained exons 3 and 2 in reversed order.

This fragment was inserted into the genome within intron 2 resulting in a genomic arrangement of exon 2, intron 2, exon 3, intron 3, the neomycin resistance cassette, a portion of intron 1, exon 2, intron 2, exon 3 and then the rest of the locus as in the wildtype allele. This construct was transfected into ES cells according to standard protocols. Neomycin-resistant colonies were selected and a second selection with 6-thio-guanine (6TG) was then applied to select for Hprt deficient cells. A number of colonies were visible and they were isolated and expanded. A resistant colony (S4 cells) was selected based on optimal cell shape and growth rate and used for production of transgenic mice. The ES cells were also analyzed for frequency of deletion events.

Hprt Based DEL Substrate

The Hprt gene has been used as selectable marker in transgenic applications (e.g. Deotschman et al. 1988, Thomas and Capecchi 1987). It has been previously shown that deletion events between two copies of a duplication of the Hprt gene are inducible after treatment with X-rays and alkylating agents in CHO cells (Zhang and Jensen 1992). Recently, we have shown that the frequency of DEL recombination in a human cell-line containing a spontaneously arisen duplication of a region of Hprt can be increased after treatment with Salmonella assay positive as well as with Salmonella assay negative carcinogens. A DEL construct based on an Hprt duplication has the advantage that the Hprt gene is stably expressed in all tissues, has a defined location on the X chromosome and its genetic and metabolic properties are very well documented. The Hprt gene is well characterized, its protein catalyzes the transfer of phosphorylated ribose to the bases hypoxanthine and guanine in the purine salvage pathway. The Hprt gene is X-linked and thus in cells derived from males there is only one copy making it a suitable system for selection for mutations. Thus, it has been studied extensively in mutation and reversion studies in mammalian cells (Stout and Caskey 1985). In addition, positive selection schemes for the wildtype as well as for the mutant are available in tissue culture. While the loss of the Hprt gene in humans results in Lesch-Nyhan disease, it is not an essential gene and mice with an Hprt mutation do not show the disease (Kuehn et al. 1987). This construct includes only a duplication of the mouse Hprt gene including one novel splice site without any bacterial or other vector sequence which provide another advantage of the Hprt duplication system.

Construction of Cells Containing the Constructs

In a preferred embodiment, the constructs are transfected into ES cells using selection for hygromycin resistance for the Geo construct and resistance to 6 thioguanine (6TG selects against Hprt product) for the Hprt construct. It is expected that 6TG resistant colonies will occur much less frequently since targeted integration into Hprt is required. These cells are used to determine the level of spontaneous and carcinogen induced deletions. G418 is used to select for deletions with cells containing the Geo construct and medium containing hypoxanthine, aminopterine and thymidine (HAT) used to select for deletions with the Hprt construct.

To determine whether deletions are inducible by carcinogens gamma rays are used. Ionizing radiation has been shown to induce deletions in yeast (Schiestl 1989) human cells (see herein) and in vivo in the mouse (Schiestl et al. 1994).

Selection Against Spontaneous Hprt+ Reversion Events

It is possible that a spontaneous deletion event could occur during development thereby producing a Hprt+/Hprt− chimeric state in the resulting transgenic mouse. Quantification of events is not possible in these animals. Therefore the following protocol is followed in order to remove revertant cells in such chimeric animals, rendering them nonchimeric.

Analysis of ES Cells
Methods for Quantification of the Frequency of Deletion Events
1. SDS-PAGE and Western Analysis Murine embryonic stem cells (ES) wildtype cells containing the duplication are assayed for the presence of the gene product. In an embodiment the Hprt duplication (designated S4 cells) are assayed for the presence of HPRT protein. Cells are lysed and extracts centrifuged in a microcentrifuge. Supernatants are used for SDS-PAGE and Western analysis using standard protocols. Protein content of the extract is determined using a BioRad kit based on the method of Bradford.

Wildtype ES cells express detectable HPRT protein of 24 kD size. S4-ES cells carrying the 7 kb duplication do not display any detectable band upon Western analysis. Therefore, transgenic mice derived from the S4-ES cells can be scored for Hprt+ revertant cells by quantification of the amount of HPRT protein in different tissues of the transgenic mouse before and after carcinogenic exposure.

Controls using liver, kidney and small intestine from Hprt null (knockout) mice display Western blots identical to those from S4-ES cells. The sensitivity of the assay is tested using serial dilutions of wildtype ES cell extracts. The HPRT protein bands are detected with as little as 300 ng of protein loaded in a gel. Therefore small numbers of revertant cells can be detected utilizing this method. Alternatively, an ELISA for HPRT+ protein with the same sensitivity can be used.

2. Enzymatic Assay

Hprt plays a role in the pathway facilitating the conversion of hypoxanthine and guanine into inosine monophosphate (IMP) and guanine monophosphate (GMP) respectively. Protein extracts from wildtype ES cells, S4-ES cells and wildtype murine tissue samples are tested for HPRT enzyme activity. The tissues used are liver, skeletal muscle, kidney and brain. The enzymatic activity of Hprt protein in the extracts is determined using $^{14}C$ hypoxanthine as the substrate. The extracts are then separated by paper chromatography. Positions to which the radioactive proteins (hypoxanthine and the products of the reaction: inosine and IMP) migrate can be visualized by UV light. These spots are then excised from the paper and the radioactivity quantitated by a scintillation counter. The activity of the Hprt enzyme per microgram of protein is calculated. Results show, as in the Western Analysis, that the wildtype ES cell extracts and wildtype tissue isolates have measurable enzymatic activity. The S4-ES cell extracts demonstrate no detectable activity. HPRT+ activity correlates with the number of Hprt revertant cells and is used in the transgenic mouse to quantify the number of reversion events.

Example 3

Inducibility of DEL Recombination in the S4 Embryonic Stem Cells that are Used to Construct the Transgenic Mouse ES cells containing a duplication in exons 2 and 3 of the Hprt gene were grown to 80% confluence in 10 cm gelatin-coated petri plates, using 6-thioguanine supplemented ES medium (DMEM, 15% FBS, 2 mM Glutamine, 2% Penicillin/Streptomycin, $1\times10^{-4}$ 2-Mercaptoethanol, $1\times10^{-4}$ Non-essential Amino Acids, and LIF).

Cells were washed 3 times with PBS and non-selective ES medium was added and cells were allowed to grow for 24 hours. Cells were then washed 3 times with PBS and 3 ml of trypsin-EDTA was added to allow cells to detach. Cells in trypsin were neutralized by adding 5 ml of ES media. Cells were thoroughly resuspended in the ES medium to break up colonies. Cells were then centrifuged at 1500 RPM and resuspended in fresh ES medium. Cells were counted and plated at a concentration 500,000 cells/10 cm petri plate. For Colony Forming Efficiency (CFE), cells were diluted and plated at 500 cells/6 cm petri plate. Cells were allowed to adhere and grow for 24 hours. Cells were then exposed to MMS at 5, 10, 20, and 40 mg/ml concentrations for 24 hours. Cells were then washed 3 times with PBS and non-selective ES medium was added and cells were incubated at 37° C. and 5% $CO_2$ for another 24 hours. HAT-supplemented ES medium was then added to the treated cells in the 10 cm plates to select for wildtype revertants. Revertant and CFE colonies were counted after 6 days of incubation at 37° C. and 5% $CO_2$. The number of revertant clones were calculated per $10^5$ viable cells which corrects for the MMS induced toxicity. Two plates per treatment point and the control were used and the data represent the average of two experiments.

As shown in Table 3, the ES cells containing the Hprt duplication responded in a dose dependent manner to exposure to Methylmethane sulfonate (MMS). This along with Example 2 provides the information for using transgenic animals carrying a duplication for Hprt.

Throughout this application, various publications, including United States patents, are referenced either by complete citation or by author and year and patents by number. Full citations for the publications cited by author and year are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

EFFECT OF X-RAYS ON REVERSION OF PINK-EYED UNSTABLE IN THE MOUSE.

| Dose | Irrad. at day of gestation | # of mice irradiated | No. of offsprings | No. of live offsprings | No. of spotted offsprings | Frequency of spotting |
|---|---|---|---|---|---|---|
| Control | | | | 498 | 28 | 5.6% |
| 1 Gy | 8.5 | 23 | 61 | 36 | 9 | 25% |
| 1 Gy | 9.5 | 24 | 62 | 56 | 12 | 19% |
| 1 Gy | 10.5 | 64 | 174 | 172 | 40 | 23% |
| Sum of irrad. | | | | 264 | 61 | 23% |

TABLE 2

EFFECT OF CARCINOGENS ON INTRACHROMOSOMAL RECOMBINATION IN MICE

| Chemical | Dose mg/kg | # of mice treated | No. of live offsprings | Average litter size | No of spotted offsprings | Frequ. | Significance p = |
|---|---|---|---|---|---|---|---|
| Control | 0 | | 585 | | 62 | 11% | |
| EMS | 100 | 21 | 94 | 4.5 | 27 | 29% | <<0.0005 |
| MMS | 100 | 22 | 83 | 3.8 | 21 | 25% | <<0.0005 |
| ENU | 25 | 18 | 57 | 3.2 | 30 | 53% | <<0.0005 |
| Corn oil contr. | 0.2 ml | 10 | 51 | 5.1 | 2 | 3.9% | |
| Benzo(a)pyrene | 150 | 10 | 32 | 3.2 | 20 | 63% | <<0.0005 |
| Trichloroethylene | 200 | 18 | 41 | 2.3 | 13 | 32% | <0.005 |
| Benzene | 200 | 15 | 48 | 3.2 | 13 | 27% | <0.01 |
| Control | 0 | | 337 | | 18 | 5.3% | |
| Na Arsenate | 20 | 17 | 56 | 3.3 | 16 | 29% | <<0.0005 |

TABLE 3

Effect of MMS Exposure on Intrachromosomal Recombination in ES Cells

| | Dose µg MMS/ml | | | |
|---|---|---|---|---|
| | Control | 5 | 10 | 20 |
| Ave. hprt+ Revertants | 74.8 | 52.0 | 80.3 | 61.3 |
| Ave. CFE | 60 | 64.5 | 45 | 24.3 |
| CFE % | 100.0% | 81.1% | 73.0% | 34.1% |
| Rev. Freq. per $10^5$ viable cells | 9.4 | 13.0 | 16.0 | 31.0 |
| Fold Induction | 1.0 | 1.4 | 1.6 | 3.1 |

REFERENCES

Abelson, P. H. (1994) Risk assessment of low-level exposures. Science 265:1507.

Agurell, et al., (1991) Genotoxic effects of ethylene oxide and propylene oxide: a comparative study, Mutat. Res., 250:229–237.

Ames and Gold (1990) Too many rodent carcinogens: Mitogenesis increases mutagenesis. Science 249:970–971.

Aubrecht et al. (1995) Carcinogens induce intrachromosomal recombination in human cells. Carcinogenesis 16(11):2841–2846.

Biard, et al. (1992) Regulation of the *Escherichia coli* lac operon expressed in human cells. Bioch. Biophys. Acta 1130:68–74.

Blochinger and Diggelman (1984) Hygromycin B phosphotransferase as a selectable marker for DNA transfer experiments with higher eucaryotic cells. Mol Cell Biol. 4(12):2929–31.

Brennan et al., (1994) Oxidative mutagens induce intrachromosomal recombination in yeast. Mut. Res. 308:159–167

Brenner, et al., (1989) Analysis of mammalian cell genetic regulation in situ by using retrovirus derived "portable exons" carrying the *Escherichia coli* lacZ gene. Proc. Natl. Acad. Sci. USA 86:5517–5521.

Brilliant, et al., (1991) Direct molecular identification of the mouse pink-eyed unstable mutation by genome scanning. Science 252:566–569.

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Calabretta, et al., (1982) Genome intability in a region of human DNA enriched in Alu repeat sequences. Nature 296:219.

Capecchi, "Altering the genome by homologous recombination" *Science* 244:1288–1292 (1989).

Carls and Schiestl (1993) Evaluation of the yeast DEL assay with ten compounds selected by the International Program on Chemical Safety for evaluation of short term tests for carcinogens. Mutation Research 320:293–303.

Copeland et al. (1983), Excision of the DBA ectopic provirus in dilute coat-color revertants of mice occurs by homologous recombination involving the viral LTRs," Cell 33:379–387.

Cortopassi, et al., (1992) A pattern of accumulation of a somatic deletion of mitochondrial DNA in aging human tissues. Proc. Natl. Acad. Sci. USA 89:7370–7374.

Davies et al., "Targeted alterations in yeast artificial chromosomes for inter-species gene transfer", *Nucleic Acids Research*, Vol. 20, No. 11, pp. 2693–2698 (1992).

Dickinson et al., "High frequency gene targeting using insertional vectors", *Human Molecular Genetics*, Vol. 2, No. 8, pp. 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Friedrich and Soriano (1991) Promoter traps in embryonic stem cells: A genetic screen to identify and mutate developmental genes in mice. Genes and Development 5:1513–1523.

Galli and Schiestl, (1995) Salmonella test positive and negative carcinogens show different effects on intrachromosomal recombination in $G_2$ cell cycle arrested yeast cells. Carcinogenesis 16(3):659–663.

Gardner, et al. (1992) The mouse pink-eyed dilution gene: Association with human Prader-Willi and Angelmann Syndromes. Science 257:1121–1124.

Gondo, et al. (1993) High-frequency genetic reversion mediated by a DNA duplication: The mouse pink-eyed unstable mutation. Proc. Natl. Acad. Sci. USA 90:297–301.

Gordon, 1989. Transgenic Animals. Intl. Rev. Cytol. 115:171–229.

Gunz et al. "Can Nongenotoxic Carcinogens Be Detected With the lacI Transgenic Mouse Mutation Assay" disclosed (at page 209)

Heddle, et al. (1983) The induction of micronuclei as a measure of genotoxicity. A report of the U.S. Environmental Protection Agency Gene-Tox Program. Mutat. Res. 123:61–118.

Huxley et al., "The human HPRT gene on a yeast artificial chromosome is functional when transferred to mouse cells by cell fusion", *Genomics*, 9:742–750 (1991).

Jakobovits et al., "Germ-line transmission and expression of a human-derived yeast artificial chromosome", *Nature*, Vol. 362, pp. 255–261 (1993).

Jeffreys et al. (1985) Nature 314:67.

Jelinek et al. (1982), Repetitive sequences in eukaryotic DNA and their expression. Annual Review of Biochemistry, 51:770–771.

Kuehn et al., (1987) A potential animal model for Lesch-Nyhan syndrome through introduction of HPRT mutations into mice. Nature 326:295–298.

Lamb et al., "Introduction and expression of the 400 kilobase precursor amyloid protein gene in transgenic mice", *Nature Genetics*, Vol. 5, pp. 22–29 (1993).

Lavitrano et al, 1989. Cell 57:717–723

Lo, 1983. Mol. Cell. Biol. 3:1803–1814

Melvold (1971). Mutation Research 12:171–174

Mirsalis, et al. (1992) Toxicologist 12:53.

Mirsalis, (1993a). Effects of nongenotoxic carcinogens or hepatic mutations in lacI transgenic mice, Environ. Mol. Mutagen. 21[22]:48.

Mirsalis, et al. (1993b). Induction of hepatic mutations in lacI transgenic mice, Mutagenesis, 8(3) :265–271.

Monnat, et al., (1992) Genomics 13:788–796.

Moore, et al., (1990) Interaction of the murine dilute suppressor gene (dsu) with fourteen coat color mutations. Genetics 125:421–430.

Murti et al., (1992) High frequency of germ line gene conversion in transgenic mice. Mol. Cell. Biol. 12:2545–2552.

Murti, et al. (1994) A recombination based transgenic mouse system for genotoxicity testing. Mutat. Res. 307:583–595.

Nagy, et al. (1993) Derivation of completely cell culture derived mice from early-passage embryonic stem cells. Proc. Natl. Acad. Sci. USA 90:8424–8428.

Nolan et al., (1988) "Fluorescence-activated cell analysis and sorting of viable mammalian cells based on beta-D-galactosidase activity after transduction of *Escherichia coli* lacZ" PNAS USA 85:2603–2607.

Paulson et al. (1985), A transposon-like element in human DNA, Nature 335:400–402

Pearson and Choi, Expression of the human β-amyloid precursor protein gene from a heast artificial chromosome in transgenic mice. Proc. Natl. Scad. Sci. USA, 1993. 90:10578–82.

Rannug, et al. (1992) Certain tryptophan photoproducts are inhibitors of cytochrome P450-dependent mutagenicity, Environm. and Molec. Mutagen. 20:289–296.

Reaume et al., 1996, Enhanced amyuloidogenic processing of the β-amyloid precursor protein in gene-targeted mice bearing the Swedish familial Alzheimer's disease mutations and a "humanized" Aβ sequence. *J. Biol. Chem.* 271(38):23380–23388.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Russell and Russell (1954) An analysis of the changing radiation response of the developing mouse embryo. J. Cellular Comp. Physiol. 43:103–149.

Russell, et al. (1981) Use of the mouse spot test in chemical mutagenesis: Interpretation of past data and recommendation for future work. Mutation Res. 86:355–379.

Schedl et al., "A yeast artificial chromosome covering the tyrosinase gene confers copy number-dependent expression in transgenic mice", *Nature*, Vol. 362, pp. 258–261 (1993).

Schiestl, (1989) Nonmutagenic carcinogens induce intrachromosomal recombination in yeast. Nature 337:285–288.

Schiestl et al., (1989) Carcinogens induce intrachromosomal recombination in yeast. Carcinogenesis 10:1445–1455.

Schiestl et al. (1997a) Carcinogens induce reversion of the mouse pink-eyed unstable mutation. PNAS 94:4576–4581.

Schiestl et al., (1994) Reversion of the mouse pink-eyed unstable mutation induced by low doses of X-rays. Science 266:1573–1576.

Schiestl and Prakash, (1988) RAD1, an excision repair gene of *Saccharomyces cerevisiae*, is also involved in recombination. Mol. Cell. Biol. 8:3619–3626.

Schlager and Dickie ( 1967) Spontaneous mutation and mutation rates in the house mouse. Genetics 57:319–330.

Schmid et al. (1989) In .Adolph, K. W. (ed.), Chromosomes: Eukaryotic, Prokaryotic and Viral., CRC Press, Boca Raton, Vol. I, pp. 3–29.

Searle and Stephenson (1982) An in vivo method for the detection of somatic mutations at the cellular level in mice. Mutat. Res. 92:205–215.

Seperak et al. (1988), Somatic and germ-line reverse mutation rates of the retrovirus-induced dilute coat-color mutation of DBA mice," PNAS USA 85:189–192.

Singer (1982), SINEs and LINES: Highly repeated short and long interspersed sequences in mammalian genomes, Cell 28:433–434.

Sommers, (1995) Induction of DEL recombination in the yeast *Saccharomyces cerevisiae* using microtiter plate assay format. In Vitro Toxicology. 8(1):37–47.

Soong, et al. (1992) Mosaicism for a specific somatic mitochondrial DNA mutation in adult human brain. Nature Genetics 2:318–323.

Stout. and Caskey (1985) HPRT: gene structure, expression, and mutation. Annu. Rev. Genet. 19:127–148.

Strauss et al., "Germ line transmission of a yeast artificial chromosome spanning the murine $\alpha_1$ (I) collagen locus", *Science*, Vol. 259, pp. 1904–1907 (1993).

Styles and Penman (1985). The mouse spot test, evaluation of its performance in identifying chemical mutagens and carcinogens. Mutation Res. 154:183–204.

Tao et al, (1993). Comparison of somatic mutation in a transgenic versus host locus. PNAS 90:10681–10685.

Thacker, (1992). Radiation induced mutation in mammalian cells at low doses and low dose rates. Advances in Radiation Biology, 16:77–124.

Thomas and Capecchi (1987) Site-directed mutagenesis by gene targeting in mouse embryo-derived stem cells. Cell 51:503–512.

Thompson et al, 1989. Cell 56:313–321

Van der Putten et al, 1985. PNAS USA 82:6148–6152

Weinstein, (1991) Mitogenesis is only one factor in carcinogenesis. Science 251:387–388.

Yang, et al. (1988) Spontaneous reversion of novel Lesch-Nyhan mutation by HPRT gene rearrangement. Somat Cell Mol Genet. 14(3):293–303.

Zakany et al. (1990) The use of lacZ gene fusions in the studies of mammalian development: developmental regulation of mammalian homeobox genes in the CNS. J. Physiol., Paris, 1990, 84:21–26.

Zhang and Jenssen (1992) Reversion of the Hprt mutant clone SP5 by intrachromosomal recombination. Carcinogenesis, 13:609–615.

What is claimed is:

1. A process for screening an agent to determine its effect upon the frequency of genome rearrangement in C57BL/6J-$p^{un}/p^{un}$ mice including the steps of:

(a) providing a pregnant C57BL/6J-$p^{un}/p^{un}$ mouse comprising a head-to-tail duplication of genetic elements in its genome, wherein the head-to-tail duplication of genetic elements is sufficiently homologous so that, under ambient conditions, they recombine with each other and give rise to an identifiable genome rearrangement resulting in reversion to a wild type gene copy at a rate of at least $1\times10^{-4}$ occurrences per cell generation, such that the offspring of the C57BL/6J-$p^{un}/p^{un}$ mouse exhibit dark patches of coat color;

(b) exposing at least one pregnant C57BL/6J-$p^{un}/p^{un}$ mouse to the agent to be tested, thereby providing an exposed mouse, wherein said exposing produces a wild type gene copy that is a product of the reversion;

(c) determining the extent of genome rearrangement resulting in reversion to a wild type gene copy in the offspring of the exposed mouse; and (d) comparing the extent of genome rearrangement resulting in reversion to a wild type gene copy in the offspring of the exposed mouse with the extent of genome rearrangement resulting in reversion to a wild type gene copy in the offspring of an unexposed mouse.

* * * * *

UNITED STATES PATENT AND TRADEMARK OFFICE
CERTIFICATE OF CORRECTION

PATENT NO.    : 6,264,915 B1  Page 1 of 1
DATED         : July 24, 2001
INVENTOR(S)   : Robert H. Schiestl It is certified that error appears in the above-identified patent and that said Letters Patent is hereby corrected as shown below:

<u>Column 1,</u>
Line 11, insert:
-- Research in this application was supported in part by a grant from the National Institutes of Health (NIH Grant No. ES06593). The Government has certain rights in the invention. --

Signed and Sealed this

Seventeenth Day of December, 2002

JAMES E. ROGAN
*Director of the United States Patent and Trademark Office*